United States Patent
Dalby Brown et al.

(10) Patent No.: US 11,643,415 B1
(45) Date of Patent: May 9, 2023

(54) RABEXIMOD COMPOUNDS

(71) Applicant: CYXONE AB, Malmö (SE)

(72) Inventors: William Dalby Brown, Søborg (DK); Laurens Adrianus Hendricus Van Pinxteren, The Hague (NL); Rienk Elibert Steendam, Amsterdam (NL); Jonathan Knibbe, Amsterdam (NL); Malin Ingrid Berthold, Djursholm (SE)

(73) Assignee: CYXONE AB, Malmö (SE)

( * ) Notice: Subject to any disclaimer, the term of this patent is extended or adjusted under 35 U.S.C. 154(b) by 0 days.

(21) Appl. No.: 17/891,462

(22) Filed: Aug. 19, 2022

(30) Foreign Application Priority Data

Dec. 9, 2021 (EP) .................................... 21213418

(51) Int. Cl.
*C07D 487/04* (2006.01)
*A61P 19/02* (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

2005/0288296 A1  12/2005  Bergman et al.

FOREIGN PATENT DOCUMENTS

| EP | 1756111 A1 | 2/2007 | |
|---|---|---|---|
| WO | 2005123741 A1 | 12/2005 | |
| WO | WO-2014140321 A1 * | 9/2014 | ......... A61K 31/4985 |
| WO | 2021250197 A1 | 12/2021 | |

OTHER PUBLICATIONS

Bansback, Ni., "How important is mode of administration in treatments for rheumatic diseases and related conditions?." Current rheumatology reports 17.6 (2015): 1-13.*
Berge, S. M., "Pharmaceutical salts."Journal of pharmaceutical sciences 66.1 (1977): 1-19.*
Gould, P.L., "Salt selection for basic drugs." International journal of pharmaceutics 33.1-3 (1986): 201-217.*
Hultqvist, M.,"Rabeximod reduces arthritis severity in mice by decreasing activation of inflammatory cells." Annals of the rheumatic diseases 69.8 (2010): 1527-1532.*
Paulekuhn, G. S., "Salt screening and characterization for poorly soluble, weak basic compounds: case study albendazole." Die Pharmazie—An International Journal of Pharmaceutical Sciences 68.7 (2013): 555-564.*
Stieger, N., "Recrystallization of active pharmaceutical ingredients." Crystallization-Science and Technology [Internet], InTech (2012): 183-201.*
Extended European Search Report dated May 11, 2022, corresponding to European Patent Application No. 21213418.3; 6 pages.

* cited by examiner

*Primary Examiner* — John M Mauro
(74) *Attorney, Agent, or Firm* — Maier & Maier, PLLC

(57) ABSTRACT

Rabeximod compounds selected from HCl salts, methane sulphonic acid salts and malonic acid salts of Rabeximod. Also, a pharmaceutical composition including a Rabeximod compound, and optionally a pharmaceutically acceptable additive. Further, a method for treatment of a mammal, such as a human subject, suffering from or diagnosed with rheumatoid arthritis, preferably moderate rheumatoid arthritis, severe rheumatoid arthritis or moderate to severe rheumatoid arthritis. The method includes administering to the mammal subject an amount of a Rabeximod compound effective to treat the rheumatoid arthritis.

12 Claims, 17 Drawing Sheets

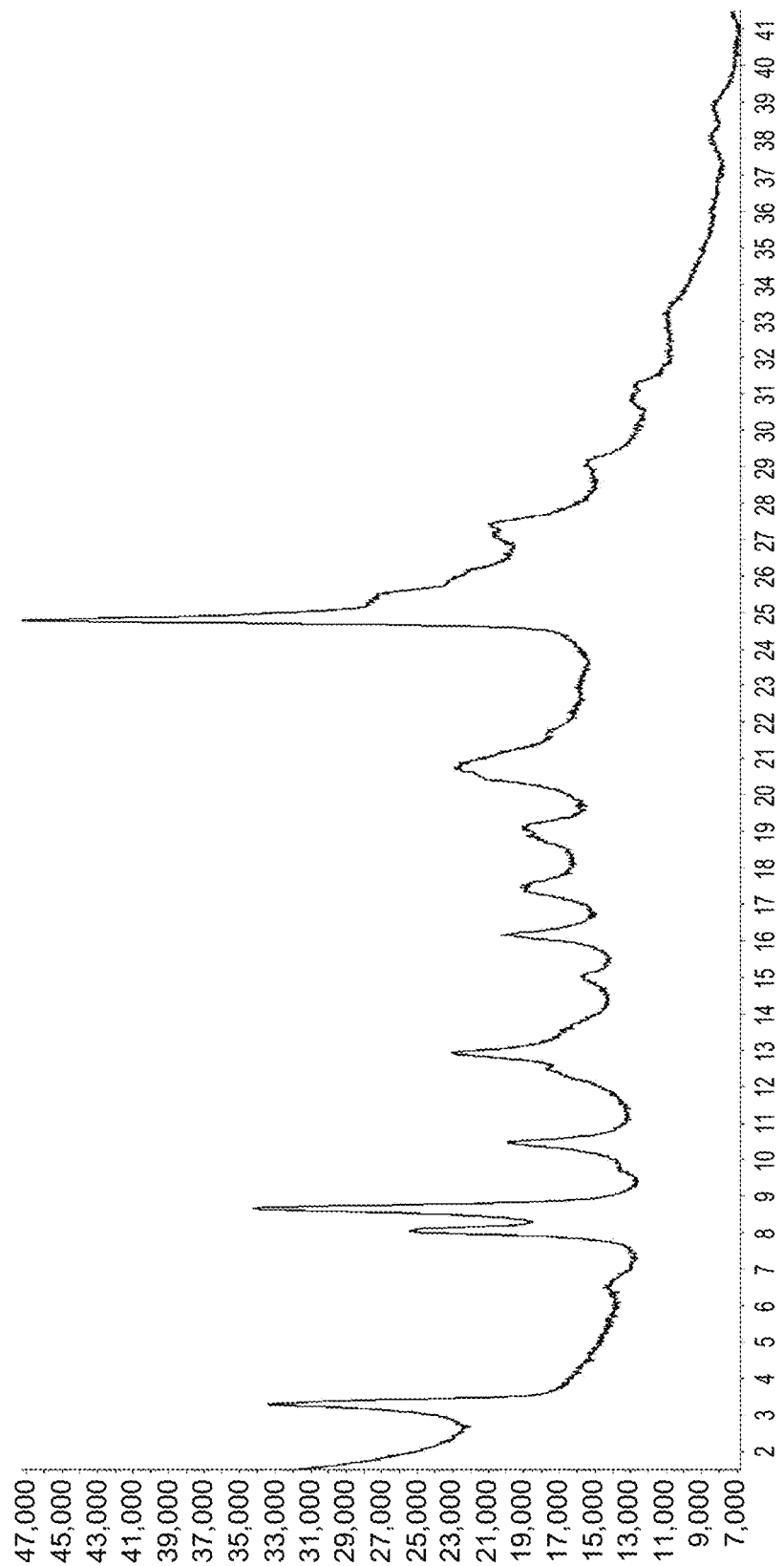

RABEXIMOD COMPOUNDS

FIELD

The present invention relates to novel Rabeximod compounds. Furthermore, the present invention concerns pharmaceutical compositions comprising of the present Rabeximod compounds. The Rabeximod compounds selected from hydrochloric acid (HCl) salt, methanesulphonic acid salt and malonic acid salt of Rabeximod are particularly useful in treating a mammal, such as a human subject, suffering from or diagnosed with, for instance, rheumatoid arthritis.

BACKGROUND

The compound known under the INN 'Rabeximod' has the IUPAC name 9-Chloro-2,3-dimethyl-6-(N,N-dimethylaminoethylamino-2-oxoethyl)-6H-indolo-[2,3-b]quinoxaline and has the following molecular structure.

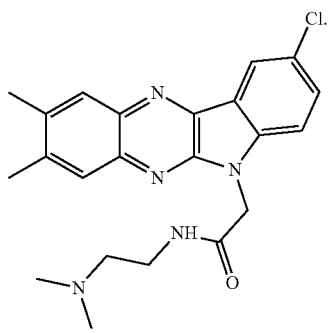 [SMILES: Cc1cc2nc3c4cc(Cl)ccc4n(CC(=O)NCCN(C)C)c3nc2cc1C]

The compound Rabeximod has been described in European patent application publication EP1756111A1 and its US counterpart US 2005/288296. The preparation of Rabeximod is specifically described in these patent publications, as compound E. The process described is a small-scale process, yielding rabeximod in free base form. Rabeximod as free base is a very stable compound and is close to insoluble in water at room temperature. EP1756111 and US 2005/288296 describe initial tests of Rabeximod (compound E) in animal models for rheumatoid arthritis and multiple sclerosis. Unpublished international application no. PCT/EP2021/065697 discloses the treatment of human RA patients by oral administration of Rabeximod (free base). Unpublished international application no. PCT/EP2021/065693 describes the use of Rabeximod (free base) in the treatment of acute respiratory syndrome, in particular acute respiratory syndrome associated with pathogenic infection, such as infection infection with influenza viruses, respiratory syncytial virus, filoviruses, arenaviruses and corona viruses.

In order to fully exploit the potential of Rabeximod in these (and other) therapeutic applications in clinical practice, it is desirable to develop Rabeximod compounds that combine more favorable pharmacokinetic ('PK') properties, such as high (relative) bio-availability, low peak-and-through variations and/or low inter-patient variability, with good manufacturing, formulation and stability attributes. Good manufacturability typically means that the compounds can be easily obtained in high purity on a large scale and in an economically viable manner. From the formulation perspective, it is required that compounds can easily be processed into the desired formulation(s), such as a solid oral dosage forms but also other types of formulations, e.g. with a view to subgroups of patients that have difficulties (or are incapable of) swallowing a solid oral formulation, such as elderly patients or patients that are oxygenated. Drug compounds of course should possess sufficient chemical and/or physicochemical stability upon storage, both as a (bulk) drug compound and as a finished drug product, and be compatible with excipients.

In practice, such objectives often proof very difficult to reconcile and there is no straight-forward approach to developing drug compounds that combine good PK properties with optimal formulation, manufacturing, and stability attributes.

It is the object of the present invention to provide new Rabeximod compounds having PK, formulation, manufacturing and/or stability attributes superior to rabeximod free base and that, overall, are more favorable candidates for actual use in clinical practice.

SUMMARY

The present invention provides new Rabeximod compounds which meet said objective. More in particular, the present invention provides Rabeximod in the form of a salt, selected from the group consisting of hydrochloric acid salt, the methane sulphonic acid salt and the malonic acid salt.

As is shown in the examples, the present Rabeximod compounds have been found to possess substantially improved (oral) bio-availability in mice, as reflected by the increase in AUC, at equal dosages. In addition, the present Rabeximod compounds have been found to produce more favorable plasma profile, upon (single) oral administration, characterized by a more gradual decrease of the plasma concentration.

The present Rabeximod compounds furthermore are considerably more water soluble than the freebase (<0.005 mg/ml). At the same time, the present Rabeximod compounds have low hygroscopocity and remain stable under exposure to variable humidity conditions.

Hence, in one aspect, the present invention relates to a compound selected from the group consisting of a HCl salt, a methane sulphonic acid (mesylate) salt and a malonic acid salt of a compound of formula (I)

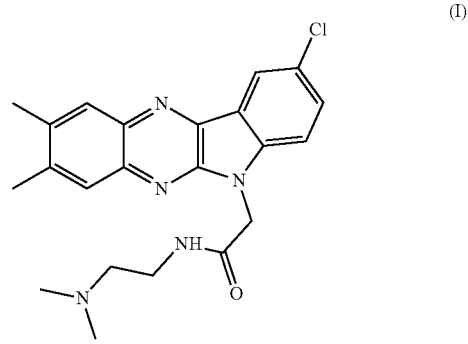 [SMILES: Cc1cc2nc3c4cc(Cl)ccc4n(CC(=O)NCCN(C)C)c3nc2cc1C]

In an embodiment the compound is a HCl salt.

In a further embodiment the compound is a methane sulphonic acid salt.

In a still further embodiment the compound is a malonic acid salt.

In further embodiments the compound of the invention is in a solid form, preferably a crystalline form, and in particular the salt is a polymorphic form.

In a further embodiment the compound is selected from a salt obtainable by the reaction of Rabeximod as free base with an acid selected from HCl, malonic acid and methane sulphonic acid.

In an embodiment, the compound is in solid and/or non-dissociated form, that is an amorphous form or a crystalline form. In another embodiment the compound is in a dissolved and/or dissociated form. In a further embodiment the compound is in crystalline form. In a still further embodiment, the compound is in a hydrated form.

In a further embodiment, the compound is selected from the salts obtainable by a reaction of Rabeximod as free base with an acid selected from HCl, malonic acid and methane sulfonic acid.

In a particular embodiment the compound is a HCl salt in crystalline form, more preferably a HCl salt in a crystalline form that is characterized by the following XRPD peaks:

| Peak number | 2θ° | d (Å) | Intensity[%] |
|---|---|---|---|
| 1 | 4.38 | 20.18 | 4 |
| 2 | 8.92 | 9.90 | 35 |
| 3 | 9.68 | 9.13 | 52 |
| 4 | 10.84 | 8.16 | 27 |
| 5 | 13.04 | 6.78 | 63 |
| 6 | 13.90 | 6.37 | 49 |
| 7 | 15.66 | 5.65 | 14 |
| 8 | 17.42 | 5.09 | 30 |
| 9 | 18.28 | 4.85 | 13 |
| 10 | 18.53 | 4.79 | 14 |
| 11 | 19.42 | 4.57 | 13 |
| 12 | 19.65 | 4.51 | 33 |
| 13 | 20.27 | 4.38 | 29 |
| 14 | 20.49 | 4.33 | 13 |
| 15 | 21.07 | 4.21 | 12 |
| 16 | 22.07 | 4.02 | 16 |
| 17 | 23.24 | 3.82 | 17 |
| 18 | 23.50 | 3.78 | 10 |
| 19 | 24.44 | 3.64 | 100 |
| 20 | 24.80 | 3.59 | 11 |
| 21 | 25.28 | 3.52 | 33 |
| 22 | 25.96 | 3.43 | 49 |
| 23 | 26.22 | 3.40 | 18 |
| 24 | 26.78 | 3.33 | 42 |

In another particular embodiment the compound is a methane sulphonic acid salt in crystalline form, more preferably a methane sulphonic acid salt in a crystalline form that is characterized by the following XRPD peaks:

| Peak number | 2θ° | d (Å) | Intensity[%] |
|---|---|---|---|
| 1 | 3.30 | 26.79 | 43 |
| 2 | 8.04 | 10.98 | 38 |
| 3 | 8.65 | 10.22 | 64 |
| 4 | 10.45 | 8.46 | 21 |
| 5 | 12.48 | 7.09 | 12 |
| 6 | 12.91 | 6.85 | 28 |
| 7 | 15.00 | 5.90 | 5 |
| 8 | 16.15 | 5.48 | 18 |
| 9 | 17.40 | 5.09 | 14 |
| 10 | 19.10 | 4.64 | 14 |
| 11 | 20.49 | 4.33 | 21 |
| 12 | 20.72 | 4.28 | 25 |
| 13 | 24.79 | 3.59 | 100 |
| 14 | 27.39 | 3.25 | 24 |

In a further particular embodiment the compound is a malonic acid salt in crystalline form, more preferably a malonic acid salt in a crystalline from that is characterized by the following XRPD peaks:

| Peak number | 2θ° | d (Å) | Intensity[%] |
|---|---|---|---|
| 1 | 6.37 | 13.87 | 64 |
| 2 | 7.12 | 12.41 | 54 |
| 3 | 8.62 | 10.25 | 56 |
| 4 | 9.96 | 8.87 | 9 |
| 5 | 10.39 | 8.51 | 20 |
| 6 | 10.88 | 8.13 | 11 |
| 7 | 12.64 | 7.00 | 2 |
| 8 | 13.08 | 6.76 | 4 |
| 9 | 13.54 | 6.54 | 4 |
| 10 | 14.25 | 6.21 | 53 |
| 11 | 14.50 | 6.10 | 22 |
| 12 | 15.46 | 5.73 | 6 |
| 13 | 15.69 | 5.64 | 5 |
| 14 | 16.25 | 5.45 | 6 |
| 15 | 16.67 | 5.31 | 6 |
| 16 | 17.26 | 5.13 | 5 |
| 17 | 18.49 | 4.80 | 18 |
| 18 | 18.86 | 4.70 | 29 |
| 19 | 19.13 | 4.64 | 48 |
| 20 | 19.54 | 4.54 | 31 |
| 21 | 21.66 | 4.10 | 16 |
| 22 | 25.36 | 3.51 | 100 |
| 23 | 21.55 | 4.12 | 24 |

In a still further embodiment the compound is obtainable by a process comprising:

a) combining, in a liquid or solvent, HCl, methane sulphonic acid or malonic acid with Rabeximod free base, to produce a solution or a suspension of the corresponding salt;

b) obtaining the salt as a solid by precipitation or crystallization, such as by cooling, evaporation of solvent, addition of an antisolvent or addition to an antisolvent, or by addition of a co-crystallizing agent, followed by filtration or centrifugation and optionally purifying the salt. Typically, the salt is obtainable by the process as described in the experimental section herein.

Each of the compounds of the present invention has a solubility in water at room temperature of above 0.3 mg/ml. Some of the compounds have a solubility in water at room temperature of at least 5 mg/ml, such as from 5-15 mg/ml.

In a further aspect, the present invention relates to a composition comprising a compound of the present invention, such as a compound according to any one of the above described embodiments. In a further embodiment said composition comprises the compound in solid and/or non-dissociated form, e.g. in case the composition is a bulk powder, a granulate or a solid finished dosage form. In a further embodiment, said composition comprises the salt in dissolved and/or dissociated form, e.g. in case the composition is a liquid finished dosage form or an aqueous solution formed and/or used in the production of solid dosage forms or the like.

In a further aspect the present invention relates to a pharmaceutical composition comprising a compound of the present invention, such as a compound according to any one of the above-described embodiments, and optionally a pharmaceutically acceptable additive.

In a still further aspect, the present invention relates to a compound of the present invention, such as a compound according to any one of the above described embodiments, for use in a method of treating a mammal, preferably a human subject, in need thereof, such as a human subject suffering from or diagnosed with rheumatoid arthritis, preferably moderate rheumatoid arthritis, severe rheumatoid arthritis or moderate to severe rheumatoid arthritis or a human subject suffering from acute respiratory syndrome that may be associated with pathogenic infection. In a still further aspect, the present invention relates to a compound of the present invention, such as a compound according to any one of the above-described embodiments, for use in a method of treating rheumatoid arthritis, preferably moderate rheumatoid arthritis, severe rheumatoid arthritis or moderate to severe rheumatoid arthritis or for treating acute respiratory syndrome that may be associated with pathogenic infection, in a mammal, such as a human subject in need thereof.

In a further aspect the present invention relates to a method for treatment of a mammal, preferably a human subject, in need thereof, such as a human subject suffering from or diagnosed with rheumatoid arthritis, preferably moderate rheumatoid arthritis, severe rheumatoid arthritis or moderate to severe rheumatoid arthritis or a human subject suffering from acute respiratory syndrome that may be associated with pathogenic infection, comprising administering to the mammal a compound of the present invention, such as a salt according to any one of the above described embodiments. In a further aspect the present invention relates to a method of treating rheumatoid arthritis, preferably moderate rheumatoid arthritis, severe rheumatoid arthritis or moderate to severe rheumatoid arthritis or a method of treating acute respiratory syndrome that may be associated with pathogenic infection, in a human subject, comprising administering to the mammal a compound of the present invention, such as a salt according to any one of the above-described embodiments.

DETAILED DESCRIPTION

Throughout the present application, the terms "Rabeximod", "rabeximod" and "9-Chloro-2,3-dimethyl-6-(N,N-dimethylaminoethylamino-2-oxoethyl)-6H-indolo-[2,3-b]quinoxaline" may be used interchangeably and mean the compound in any solid form or liquid form unless otherwise indicated or implied under the given circumstances.

Rabeximod can be obtained from the process as described in EP1756111A1 and US2005/288296, and then purified and isolated. Furthermore, Rabeximod free base as crystalline form may be obtained as described in European Patent application no. 20179279.3 (not published)

Several HCl, Mao and Mes salts of Rabeximod have been crystalized, yielding new salt forms with improved physicochemical properties compared to the rabeximod freebase. These rabeximod compounds possess a very advantageous combination of properties with regard to solubility, crystallinity, physical stability, thermal behavior, processability and hydration nature, as is illustrated by the experiments described in the experimental section.

As used herein the term "counterion" means an acid counterion which forms a salt with the protonated Rabeximod free base. When a Rabeximod salt is described herein it may be referred to using a three-letter code which identifies the counterion.

The table below lists and defines each of the specific 3-letter codes used in this document. The use of the 3-letter code identifies the salt of Rabeximod, e.g. the hydrochloric acid salt of Rabeximod is indicated by the code HCl. The description of a Rabeximod salt, such as HCl, comprises the salt in any form, such as solid, amorphous, dissolved, or polymorphic.

| 3-letter code | meaning |
| --- | --- |
| HCl | Hydrochloric acid |
| Mao | Malonic acid |
| Mes | Methane sulfonic acid |

As mentioned above, the compositions and particularly pharmaceutical compositions as herein disclosed may, in addition to the compounds herein disclosed, further comprise at least one pharmaceutically acceptable adjuvant, diluent, excipient and/or carrier. Such pharmaceutically acceptable adjuvant, diluent, excipient and/or carrier may without limitation be selected from the group consisting of Oleic acid, Tween 80, sodium carboxy methylcellulose.

In some embodiments, the pharmaceutical compositions comprise from 1 to 99 weight % of said at least one pharmaceutically acceptable adjuvant, diluent, excipient and/or carrier and from 1 to 99 weight % of a compound of formula I as herein disclosed. The combined amount of the active ingredient and of the pharmaceutically acceptable adjuvant, diluent, excipient and/or carrier may not constitute more than 100% by weight (100% w/w) of the composition, particularly the pharmaceutical composition.

In accordance with the various aspects of the invention, the composition is preferably provided in the form of a unit dosage form. The term 'unit dosage form' refers to a physically discrete unit suitable as a unitary dosage for human subjects, each unit containing a predetermined quantity of active material calculated to produce the desired therapeutic effect in association with any suitable pharmaceutical carrier(s) and/or excipient(s). Exemplary, non-limiting unit dosage forms include a tablet (e.g., a chewable tablet), caplet, capsule (e.g., a hard capsule or a soft capsule), etc. In accordance with preferred embodiments of the invention, the unit dosage form, is a unit dosage form that is suitable for oral administration. Most preferably, it is a solid unit dosage form, such as a tablet or capsule, most preferably a capsule, such as a standard gelatin capsule, which is filled with a powder as defined herein elsewhere.

In other embodiments of the invention, the present rabeximod compounds may be provided in the form of a liquid oral formulation. Liquid oral formulations are a preferred or required oral dosage form for patients that have difficulty swallowing. Liquid oral formulations require a stable, dissolved, or suspended form of the drug that meets release, bioavailability, stability and taste requirements.

In other embodiments of the invention, the present rabeximod compounds may be provided in the form of a sterile liquid suitable for parenteral administration, such as administration by iv injection or infusion. Such parenteral formulations may be the preferred or required dosage form for patients suffering severe respiratory conditions, e.g. patients that are intubated and kept in an induced coma. Sterile parenteral formulations require a stable, dissolved, or suspended form of the drug that meets release, bioavailability, and stability requirements.

It is within the purview of those of average skill in the art to conceive and develop suitable formulations, based on the present teachings and relying on the common general knowledge as reflected in text books such as Remington's Pharmaceutical Sciences (Meade Publishing Co., Easton, Pa., 20th Ed., 2000), the entire disclosure of which is herein incorporated by reference.

In a broad aspect, the present invention also relates to methods of treating a subject in need thereof, said treatment comprising the administration to said subject of a Rabeximod compound of the present invention, preferably a composition, formulation or unit dosage form comprising said rabeximod compound, as defined herein. In preferred embodiments of the invention, the subject to be treated is a human subject, preferably a human.

In a first embodiment, the present invention also relates to methods of treating a subject suffering from and/or diagnosed with rheumatoid arthritis, or a related condition, wherein the methods comprise the administration of a rabeximod compound of the instant invention.

In a further embodiment, the present invention also relates to methods of treating a subject suffering from an acute respiratory syndrome, optionally associated with a pathogenic infection, such as a corona virus infection, wherein the methods comprise the administration of a rabeximod compound of the instant invention.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to pre-vent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

Specific embodiments of the process for producing the present compounds are described in the experimental section here-in, and each individual process as well as each starting material constitutes embodiments that may form part of embodiments.

The term "and/or" as used herein is intended to mean both alternatives as well as each of the alternatives individually. For instance, the expression "xxx and/or yyy" means "xxx and yyy"; "xxx"; or "yyy", all three alternatives are subject to individual embodiments.

As used herein "pharmaceutically acceptable additive" is intended without limitation to include carriers, excipients, diluents, adjuvant, colorings, aroma, preservatives etc. that the skilled person would consider using when formulating Rabeximod in order to make a pharmaceutical composition.

The adjuvants, diluents, excipients and/or carriers that may be used in the composition of the invention must be pharmaceutically acceptable in the sense of being compatible with Rabeximod and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permit-ted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

BRIEF DESCRIPTION OF FIGURES

FIG. 3 illustrates XRPD Diffractogram for the crystalline Mes salt form prepared.

EXAMPLES

Figure 1:
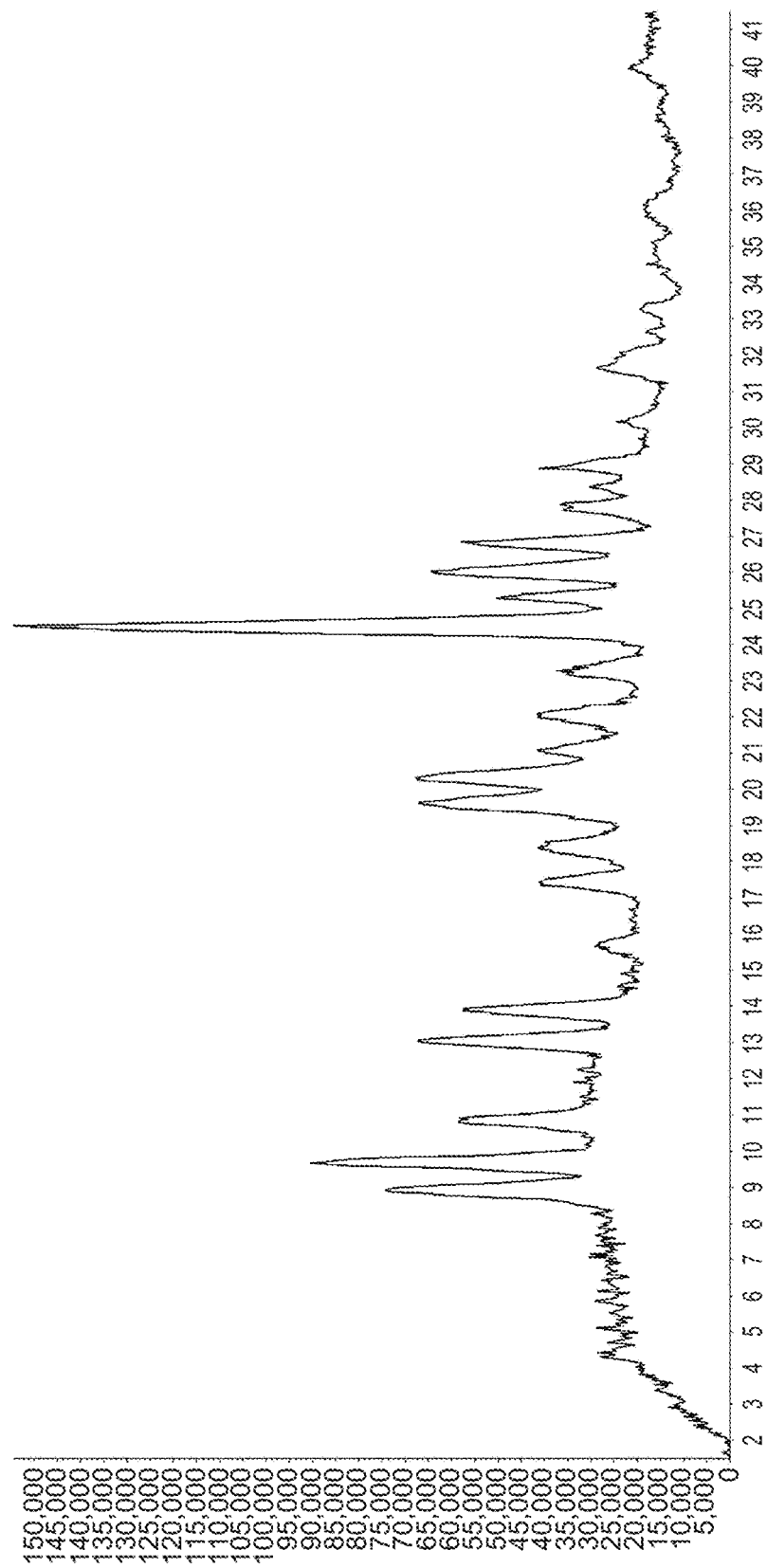
FIG. 1 illustrates the XRPD Diffractogram for the crystalline HCl salt form prepared.
Figure 2:
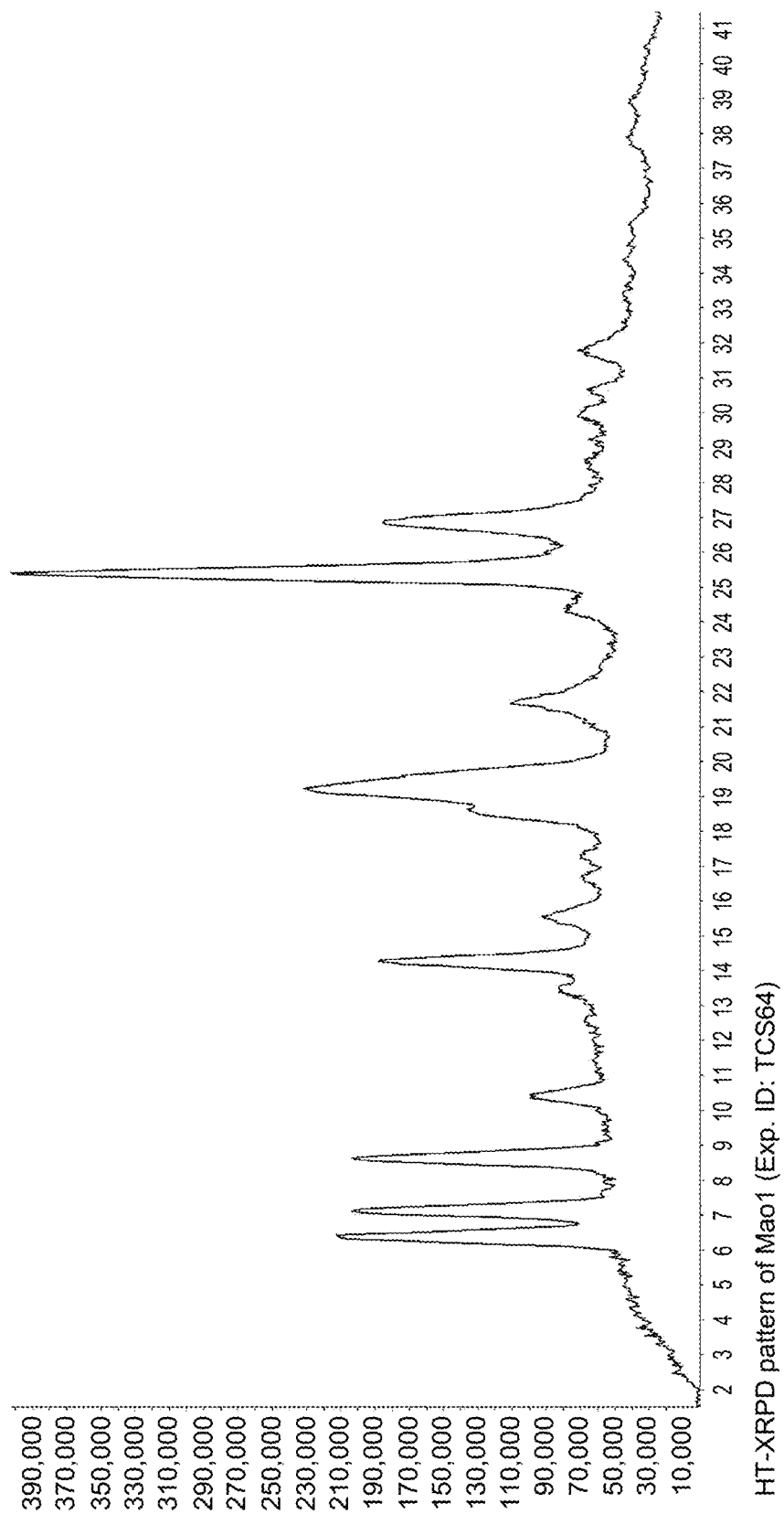
FIG. 2 illustrates XRPD Diffractogram for the crystalline Mao salt form prepared.

General Experimental Information
General abbreviations
$^1$H-NMR Proton Nuclear Magnetic Resonance
$^{13}$C-NMR Carbon-13 Nuclear Magnetic Resonance
AAC Accelerated Aging Conditions (40° C. and 75% RH)
Am Amorphous
APT Attached Proton Test
API Active Pharmaceutical Ingredient
DSC Differential Scanning calorimetry
GEN Experiment ID for amorphous feasibility tests
HR-XRPD High Resolution X-Ray Powder Diffraction
HT-XRPD High Throughput X-Ray Powder Diffraction
LCMS High-Performance Liquid Chromatography coupled with Mass Spectroscopy
MS Mass Spectroscopy
Pc Poor crystallinity
PAMPA Parallel Artificial Membrane Permeability Assay
PLM Polarized Light Microscopy
RF Response Factor RH Relative Humidity
RT Room Temperature
Ssm Experiment ID for the salt crystallization experiments under isothermal conditions
TCS Experiment ID for the salt crystallization experiments involving thermocycling
TGMS Thermogravimetric Analysis coupled with Mass Spectroscopy
Chemicals
Ace Acetone
AcN Acetonitrile
EtOH Ethanol
IPA Isopropanol, 2-Propanol
MeOH Methanol
MEK Methyl Ethyl Ketone
THF Tetrahydrofuran
Analytical Methods
X-ray Powder Diffraction XRPD patterns were obtained using a high-throughput XRPD set-up. The plates were mounted on a Bruker General Area Detector Diffraction System (GADDS) equipped with a VANTEC-500 gas area detector corrected for intensity and geometric variations. The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90s for each frame. No background subtraction or curve smoothing was applied to the XRPD patterns.

High Resolution X-Ray Powder Diffraction Measurement

The HR-XRPD data were collected on D8 Advance diffractometer using Cu $K_{\alpha1}$ radiation (1.54056 Å) with germanium monochromator at RT. Diffraction data were collected in the 2θ range 2-41.5° 2θ. Detector scan on solid state LynxEye detector was performed using 0.015° per step with 10 sec/step scan speed. The samples were measured in 8 mm long glass capillary with 0.5 mm outer diameter.

TGA/SDTA and TGMS Analysis

Mass loss due to solvent or water loss from the crystals was determined by TGA/DSC. Monitoring the sample weight, during heating in a TGA/DSC 3+ STARe system (Mettler-Toledo GmbH, Switzerland), resulted in a weight vs. temperature curve and a heat flow signal. The TGA/DSC 3+ was calibrated for temperature with samples of indium and aluminum. Samples (circa 1 mg) were weighed in 100 µL aluminum crucibles and sealed. The lids were pin-holed, and the crucibles heated in the TGA from 25 to 300° C. at a heating rate of 10° C./min. Dry $N_2$ gas was used for purging.

The gases coming from the TGA samples were analyzed by a mass spectrometer Omnistar GSD 301 T2 (Pfeiffer Vacuum GmbH, Germany). The latter is a quadrupole mass spectrometer, which analyzes masses in the temperature range of 0-200 amu.

DSC Analysis

Thermal events were obtained from DSC thermograms, which were recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 1 mg) were sealed in standard 40 µL aluminum pans, pin-holed and heated in the DSC from 25° C. to 300° C., at a heating rate of 10° C./min if not specified differently. Dry $N_2$ gas, at a flow rate of 50 mL/min was used to purge the DSC equipment during measurement.

cDSC Analysis

The cycling DSC's were measured in standard 40 µL aluminum pans, pin-holed and heated in the DSC from 25° C. to variable temperatures, then cooled back to 25° C. The heating and cooling rate was 10° C./min. Dry $N_2$ gas, at a flow rate of 50 mL/min was used to purge the DSC equipment during measurement. After the experiments, the solids were removed from the pans and analyzed by HT-XRPD.

Polarized Light Microscopy

The polarized light microscopy pictures were collected with a Leica DM 2500M optical microscope. The sample was mounted on a glass slide and measured as a dry solid.

LCMS Analytical Methods

| LC parameters: | |
|---|---|
| Instrument | Agilent 1290 series with diode array UV detector and MSD XT single quad mass detector |
| Mobile phase A | 10 mM Ammonium acetate in water |
| Mobile phase B | Acetonitrile |
| Column | Agilent Eclipse Plus C18 HD (50 × 2.1 mm; 1.8 µm) |
| Detection: | UV at 274 nm, bandwidth 4 nm, UV spectrum 200 to 400 nm. MS in positive scan mode 100-1000 m/z, 250 ms scan time |
| Flow: | 0.6 mL/min. |
| Run time | 3.5 minutes |
| Injection volume | 1.0 µL |
| Column temp. | 40° C. |
| Autosampler temp. | Ambient |

| Gradient: | Time [min.] | Gradient: | Time [min.] |
|---|---|---|---|
| | 0 | 95 | 0 |
| | 0.1 | 95 | 0.1 |
| | 2.5 | 10 | 2.5 |
| | 2.55 | 10 | 2.55 |
| | 2.56 | 95 | 2.56 |
| | 3.5 | 95 | 3.5 |

| Sample | Concentration: ca. 0.2 mg/mL Solvent: methanol |
|---|---|

The compound integrity was expressed as a peak-area percentage, calculated from the area of each peak in the chromatogram, except the 'injection peak', and the total peak-area, as follows:

$$\text{peak area}(\%) = \frac{\text{peak area}}{\text{total area of all peaks}} \cdot 100\%$$

The peak area percentage of the compound of interest is employed as an indication of the purity of the component in the sample.

For the HPLC assay, a solution of Rabeximod (SM) was measured as a reference and the peak area was assigned to 100% recovery after taking into account the amount of solvent determined by TGMS. Samples of the salts were measured in the same way and the % recovery was calculated again by taking into account the amount of solvent. With all measured salts, <100% recovery could be assigned to the API and the remaining % recovered could be assigned to the counterion from which the ratio API:counterion could be determined.

$^1$H-NMR $^1$H-NMR spectroscopy in DMSO-$d_6$ was used for compound integrity characterization and to determine the stoichiometry of the salts. The spectra were recorded at room temperature (32 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

$^{13}$C-NMR $^{13}$C-NMR-APT spectroscopy in DMSO-$d_6$ was used for compound integrity characterization. The spectra were recorded at room temperature (2048 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

Dynamic Vapor Sorption

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with a few milligrams of sample, with an accuracy of 0.1 µg. The relative humidity was varied during sorption-desorption-sorption (40-95-0-40% RH) at a constant temperature of 25° C. Weight equilibration per step was set at dm/dt <0.0002 mg/min for a minimum of 1 hour or maximum of 6 hours. Afterwards the sample was measured by HT-XRPD.

The hygroscopicity was classified according to the European Pharmacopoeia Hygroscopicity classification. Water uptake percentage at 25° C./80%RH (24h) is:

Change in mass <0.2%—Non-hygroscopic
Change in mass >0.2% & <2%—Slightly hygroscopic
Change in mass >2% & <15%—Moderately hygroscopic
Change in mass >15%—Very hygroscopic A specific crystalline form of Rabeximod free base was designated 'Form 1'. Form 1 was an anhydrous material melting at 260° C. The chemical purity of the starting material was high as determined by 1 H-NMR and LCMS. Form 1 was slightly hygroscopic and remained physically stable upon exposure to relative humidity values between 0-95%.

EXAMPLE 1: PREPARATION OF COMPOUNDS OF THE INVENTION

Materials and Methods

All chemicals were obtained from Fisher Scientific or Sigma Aldrich. Chemicals used are at least of research grade. Solvents used for the UPLC analysis are of HPLC grade.

Salt Formation and Crystallization

Figure 5:
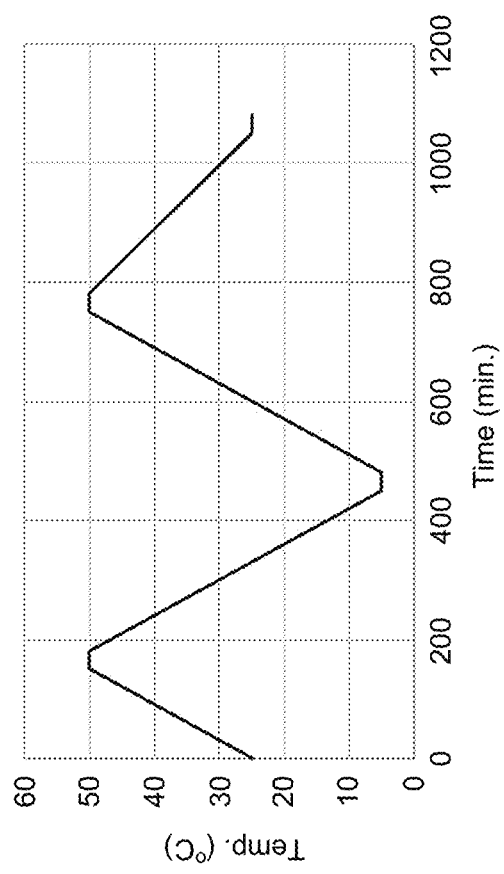
FIG. 5 shows temperature profiles which were applied in the hydrochloride acid and malonic acid salt crystallization experiments. The temperature was changed between 5-50° C. at a rate of 0.17° C./min. The initial and final temperature was 25° C.
Figure 4:
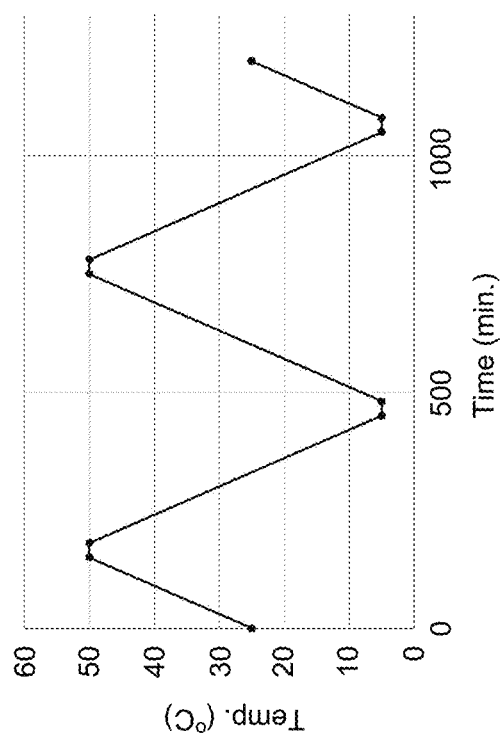
FIG. 4 shows temperature profiles which were applied in the methanesulfonic acid salt crystallization experiments. The temperature was changed between 5-50° C. at a rate of 0.17° C/min. The initial and final temperature was 25° C.
Figure 6:
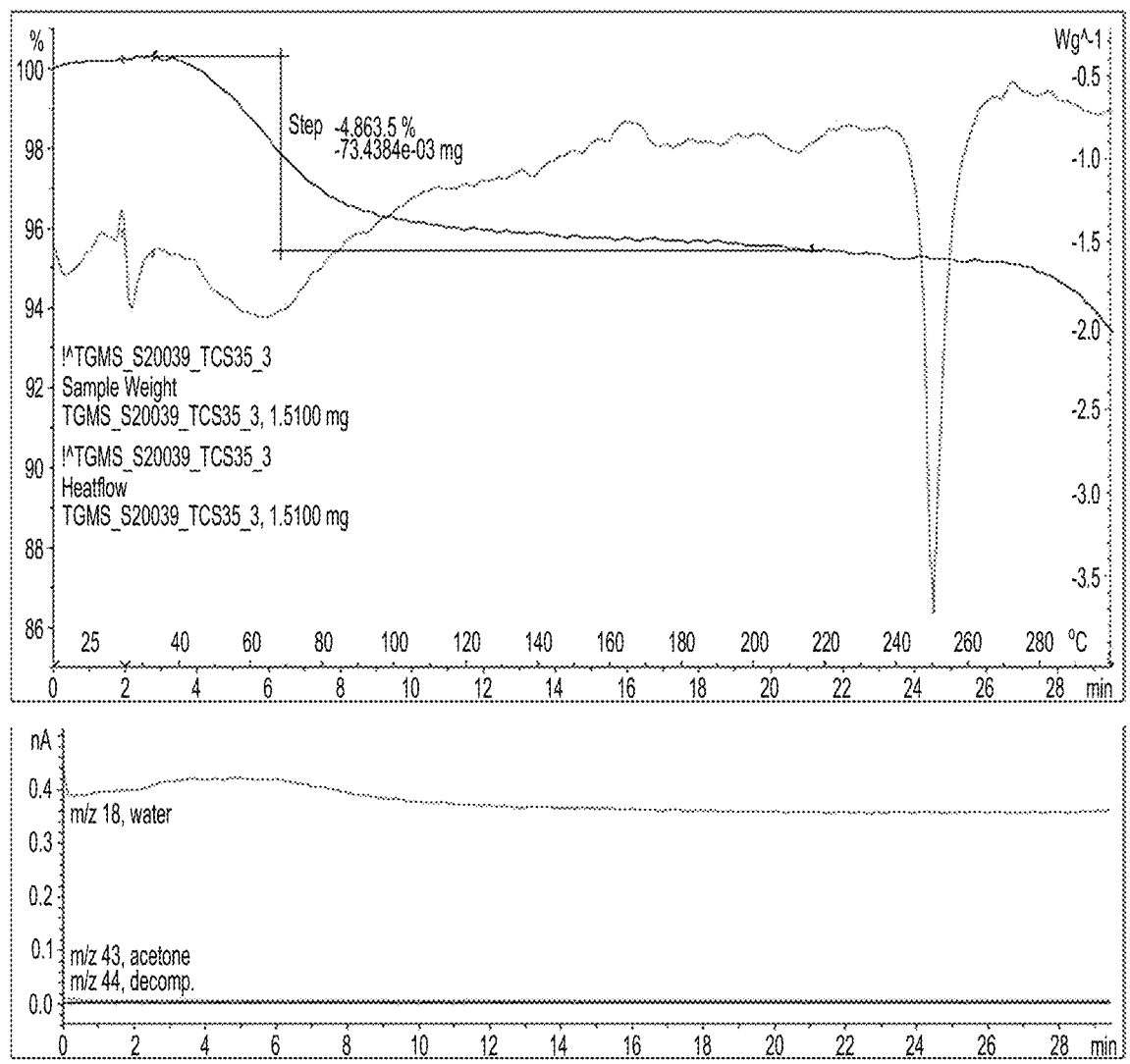
FIG. 6 shows TGMS analysis between 25-300° C. (heating rate 10° C./min) of the Mes salt (Exp. ID: TCS35). A mass loss of 4.9% was measured between 25-220° C.
Figure 7:
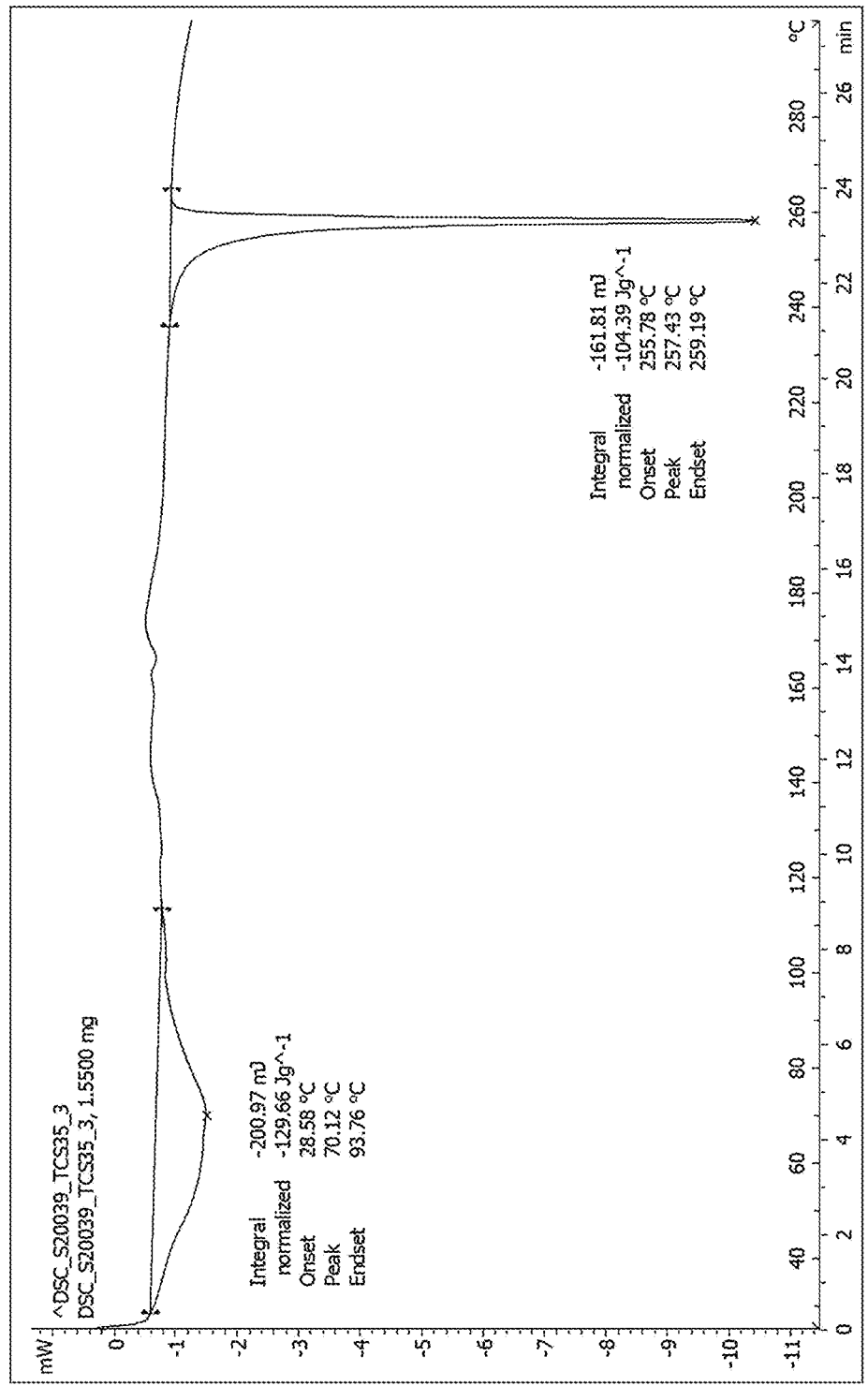
FIG. 7 shows DSC trace between 25-300° C. (heating rate 10° C./min) of the Mes salt (Exp. ID: TCS35). The endothermic event between RT-110° C. may be attributed to loss of water. Melting of the API may be associated to the sharp endothermic event at 257° C.
Figure 8:
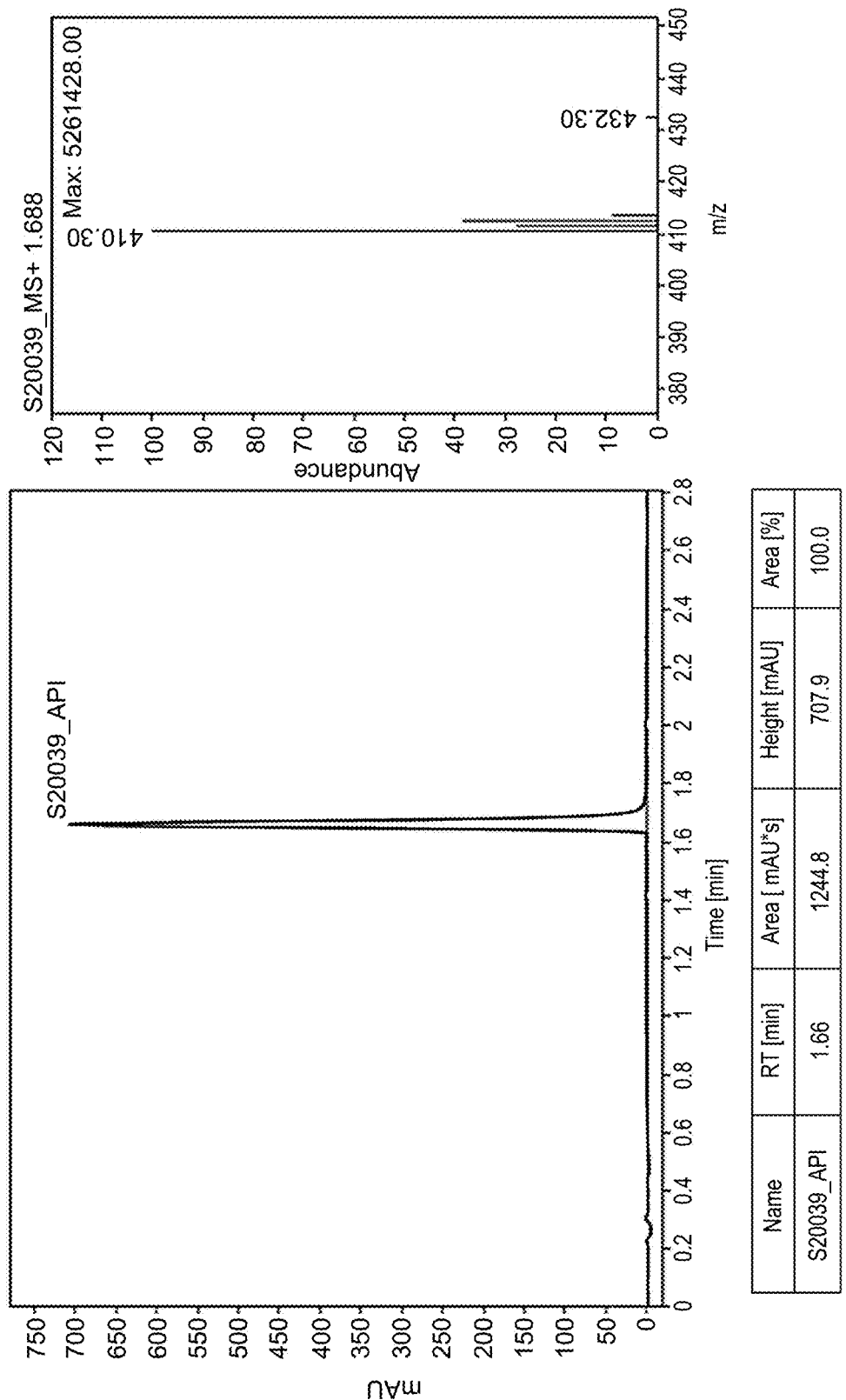
FIG. 8 shows LCMS chromatogram of the Mes salt (Exp. ID: TCS35). The API had a retention time of 1.66 min. The MS spectrum confirmed the molecular mass of the compound of 409.9 g/mol with [M+H]+ions of m/z 410.3.
Figure 9:
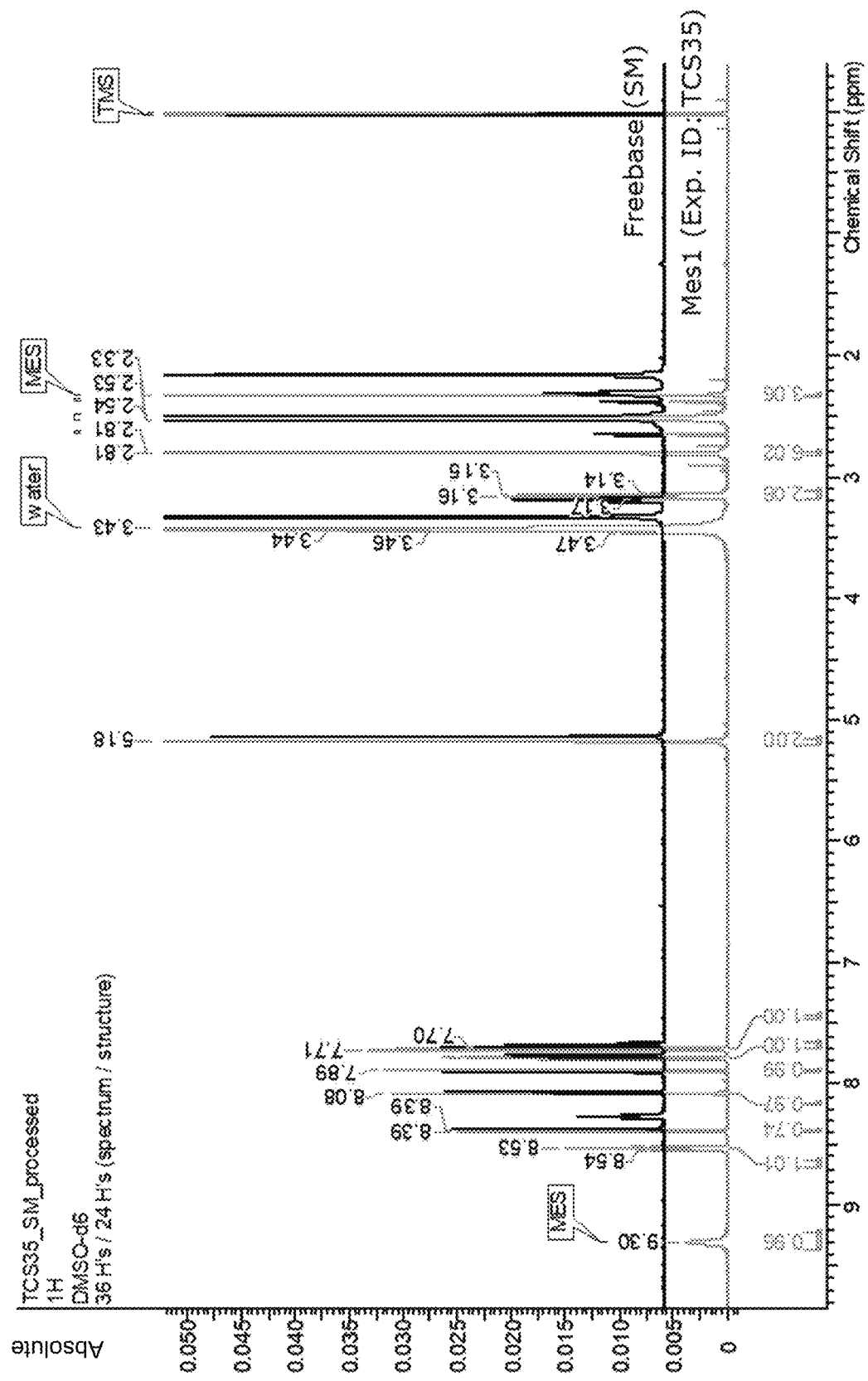
FIG. 9 shows $^{13}$C-NMR spectrum of the Mes salt (Exp. ID: TCS35, top) and the freebase (SM, top) measured in DMSO-$d_6$. In addition to Rabeximod, water (3.4 ppm), DMSO (2.5 ppm) and methanesulfonic acid ($CH_3$ at 2.53 ppm and OH at 9.3 ppm) signals were detected.
Figure 10:
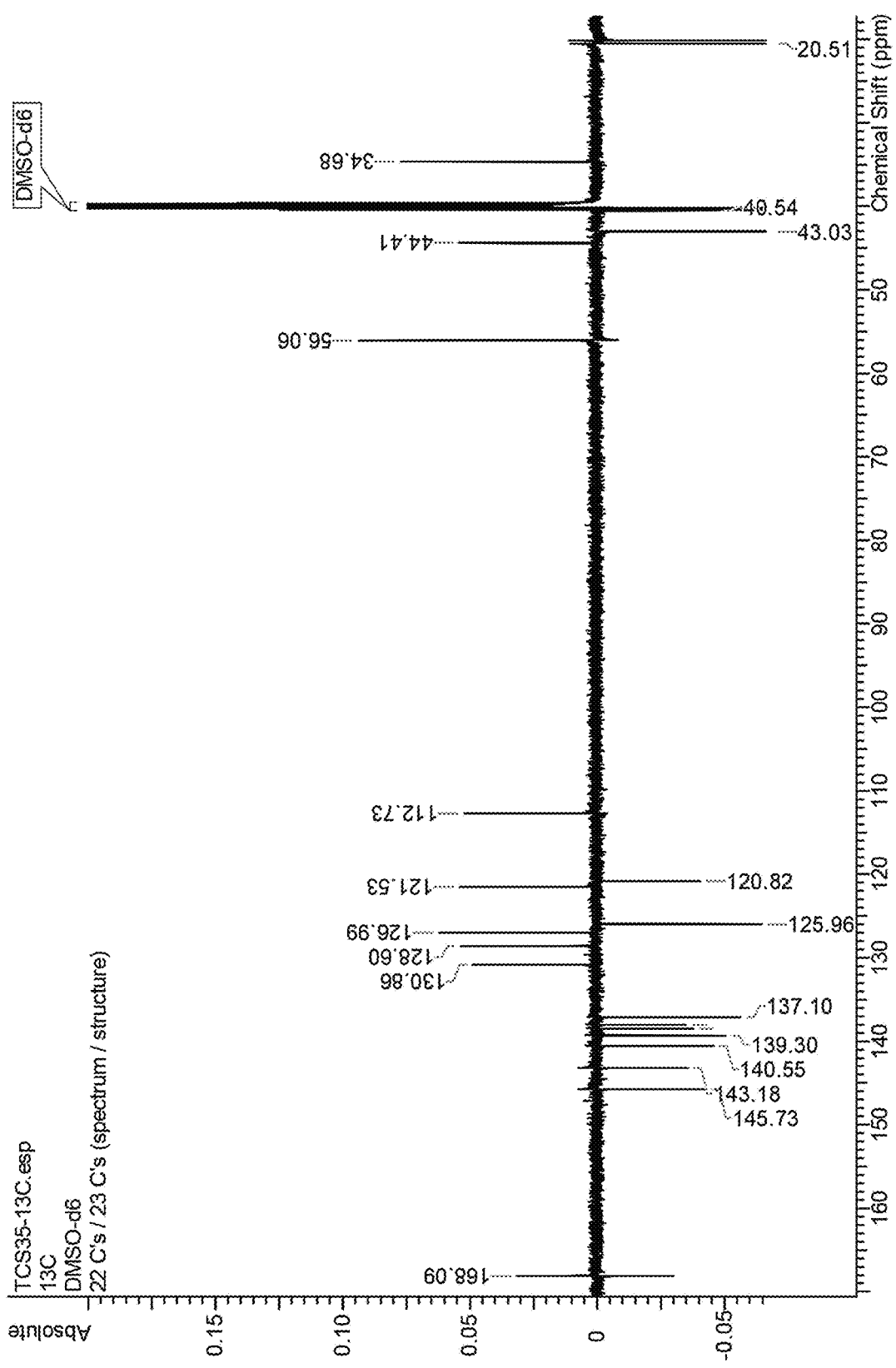
FIG. 10 shows $^{13}$C-NMR-APT spectrum of the Mes salt (Exp. ID: TCS35) measured in DMSO-$d_6$. The CH and $CH_3$ groups are positive signals whereas the $CH_2$ and quaternary carbons are negative signals. In addition to the API, signals of methanesulfonic acid and DMSO are present.
Figure 11A:
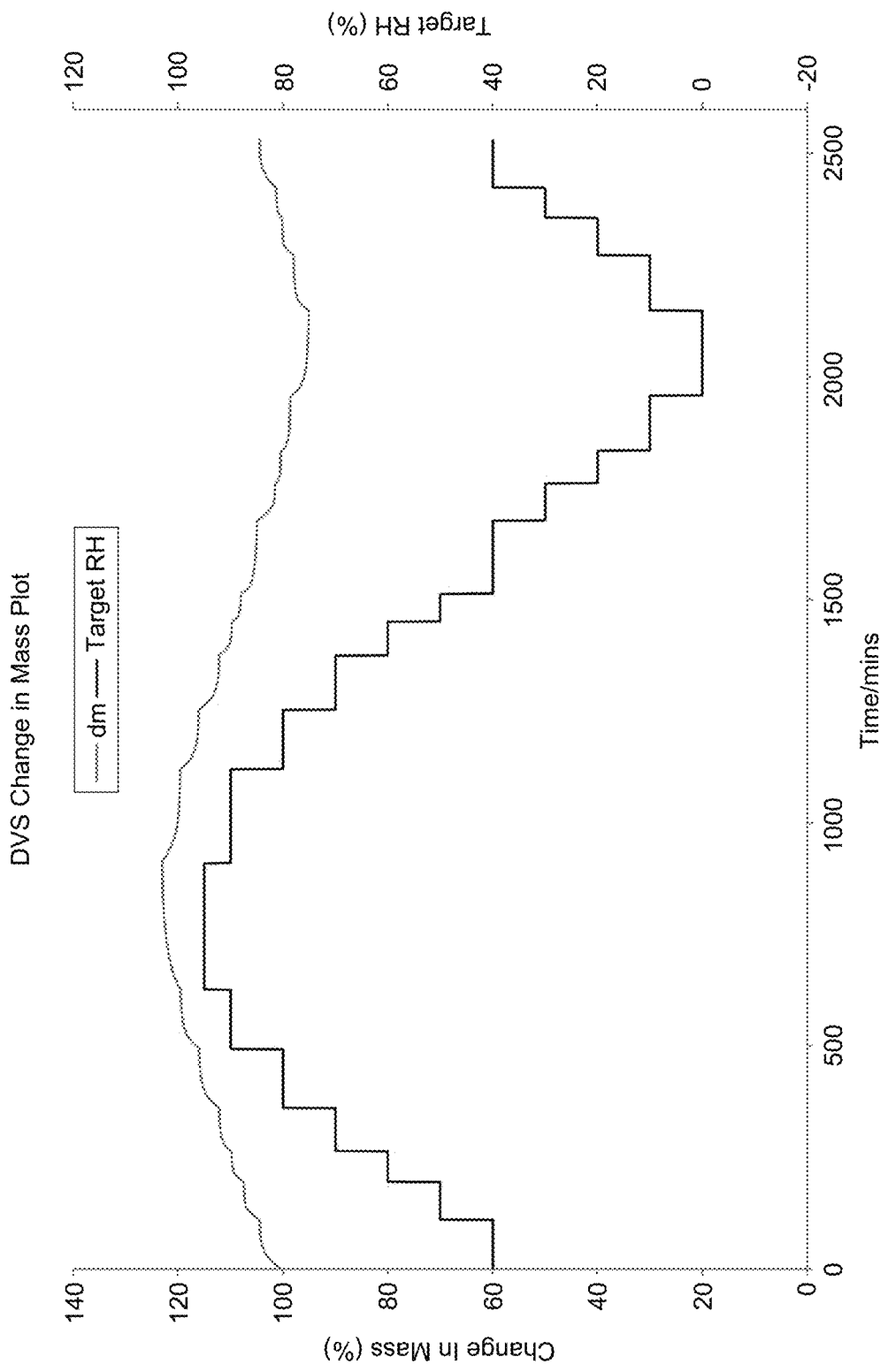
FIG. 11A and B shows Moisture Sorption Kinetic (A) and isotherm (B) plots for the Mes salt (Exp. ID: TCS35) with a first sorption cycle from 40% RH to 95% RH followed by desorption from 95% RH to 0% RH and sorption from 0% RH to 40% RH in steps of 10% RH with a minimum stage time of 10 min and maximum stage time of 6 hours.
Figure 11B:
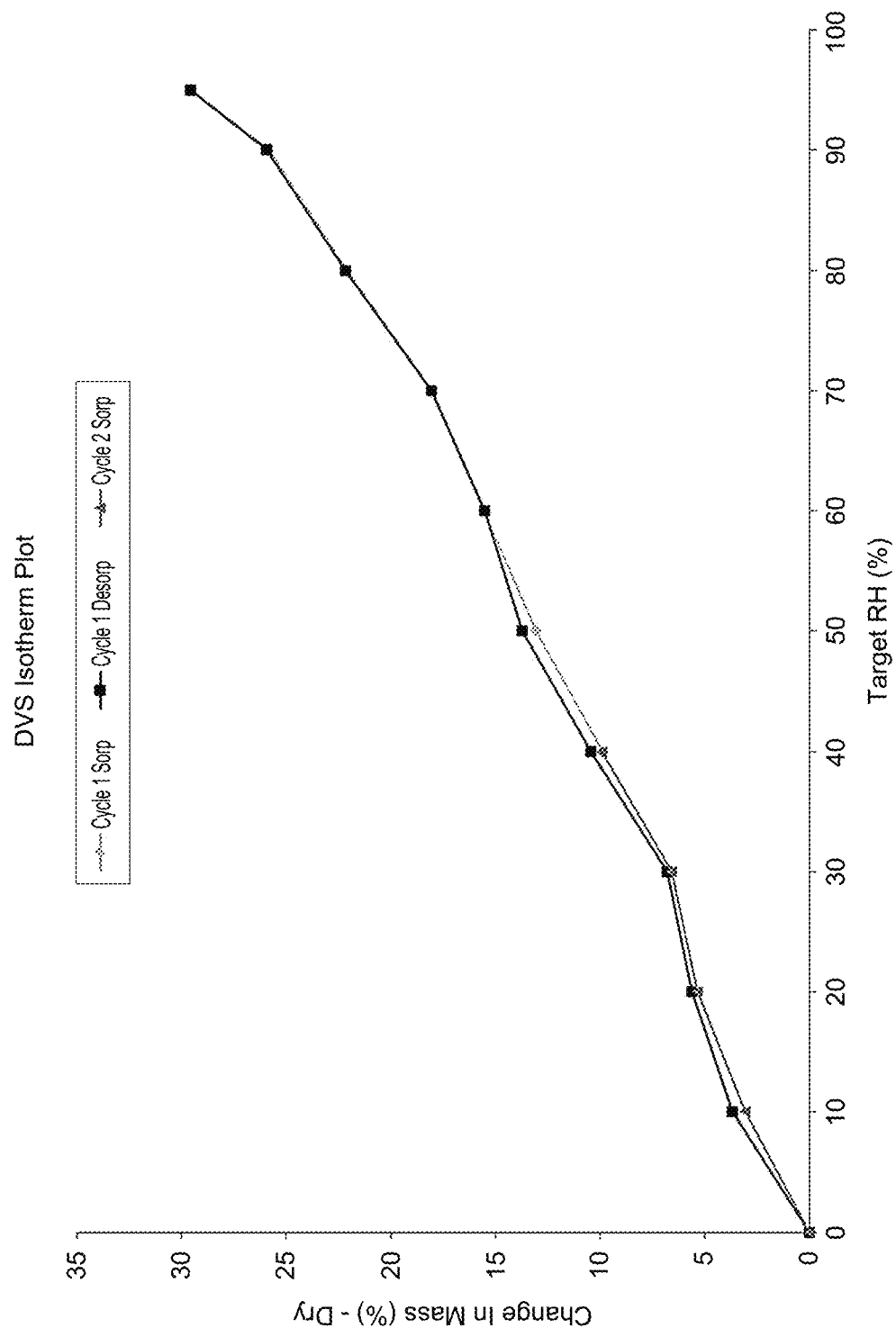
Figure 12:
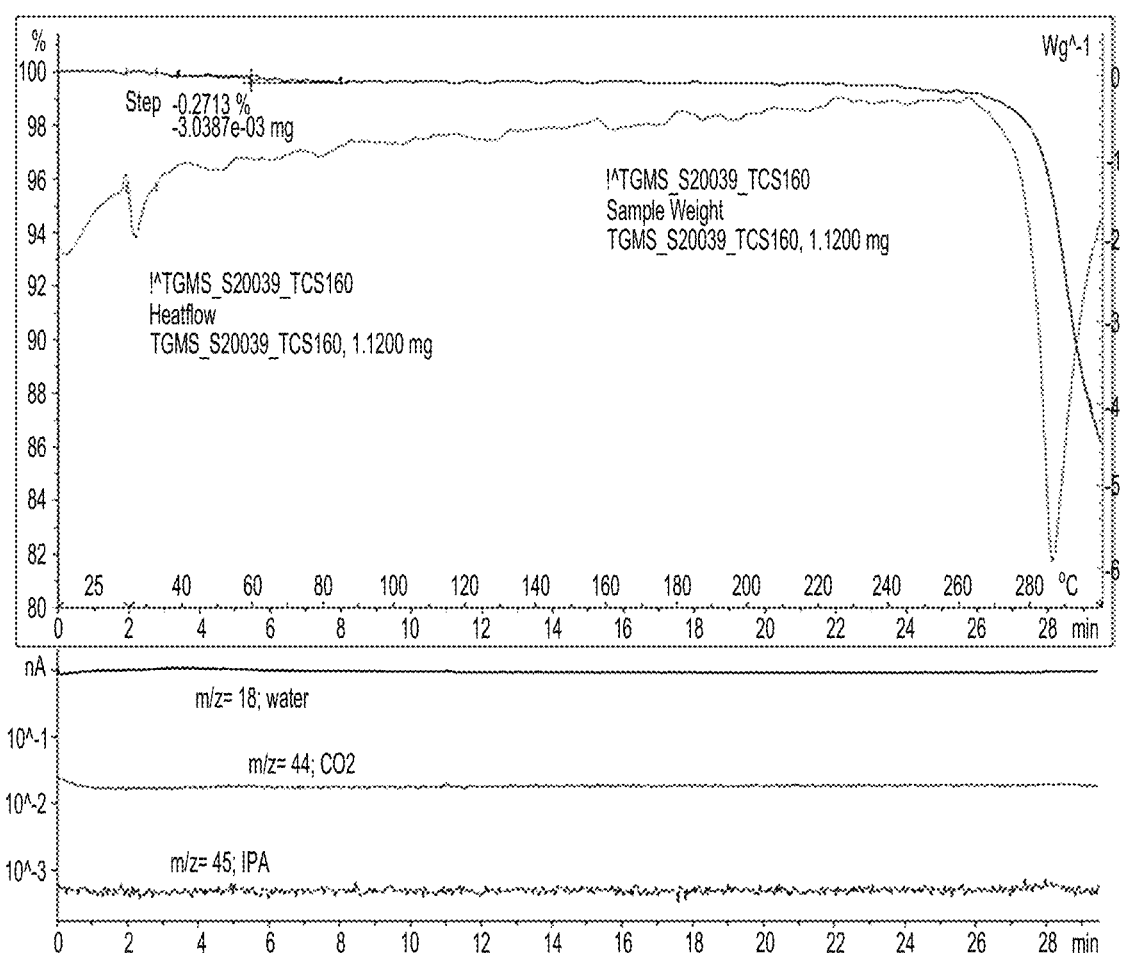
FIG. 12 shows TGMS analysis between 25-300° C. (heating rate 10° C./min) of the HCl salt (Exp. ID: TCS160). Approximately 0.3% mass loss was recorded between ~25-80° C. The endothermic event at 285° C. most likely denotes melting.
Figure 13:
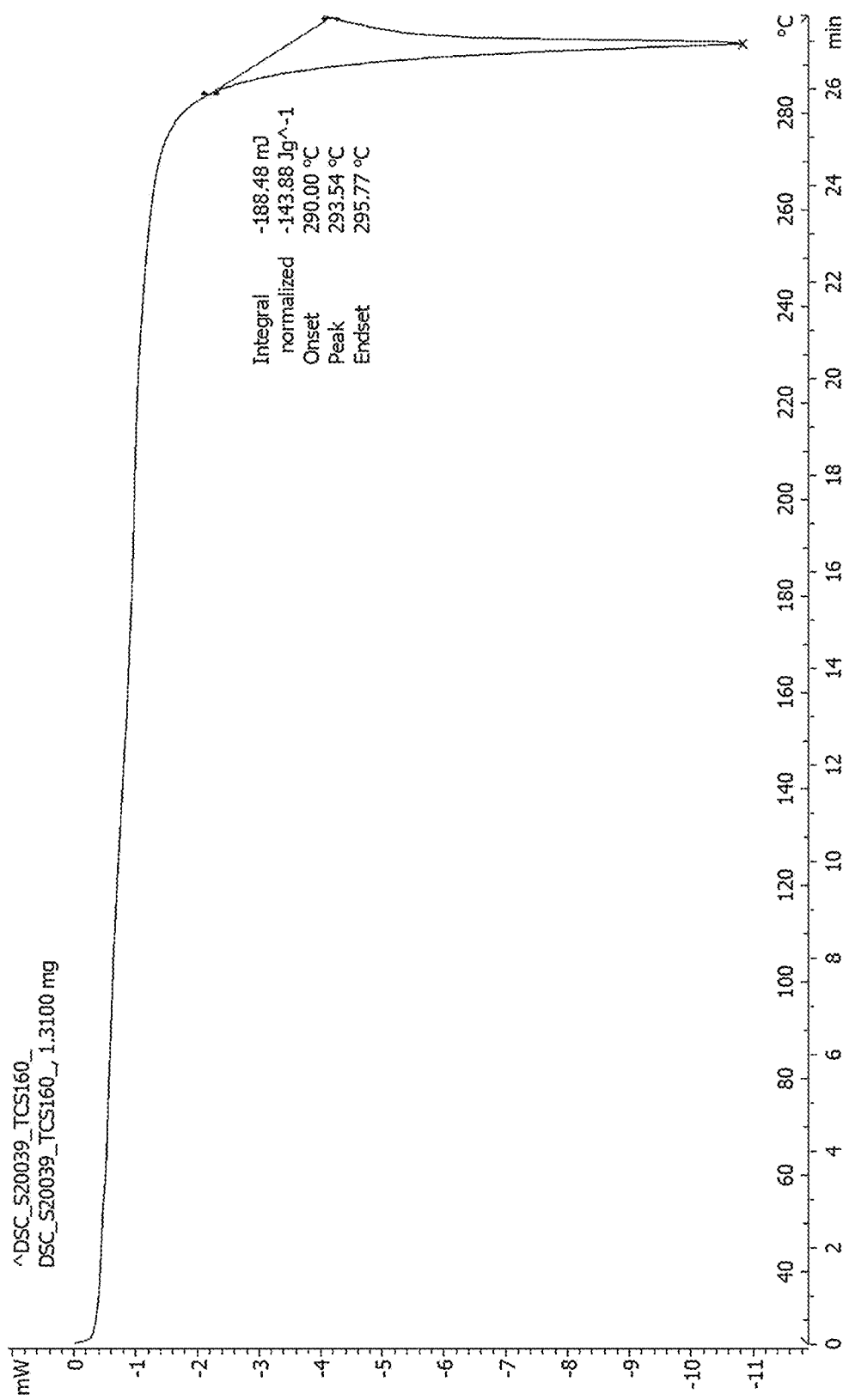
FIG. 13 shows DSC trace between 25-300° C. (heating rate 10° C./min) of the HCl salt (Exp. ID: TCS160). Melting of the API may be associated to the sharp endothermic event at 294° C.
Figure 14:
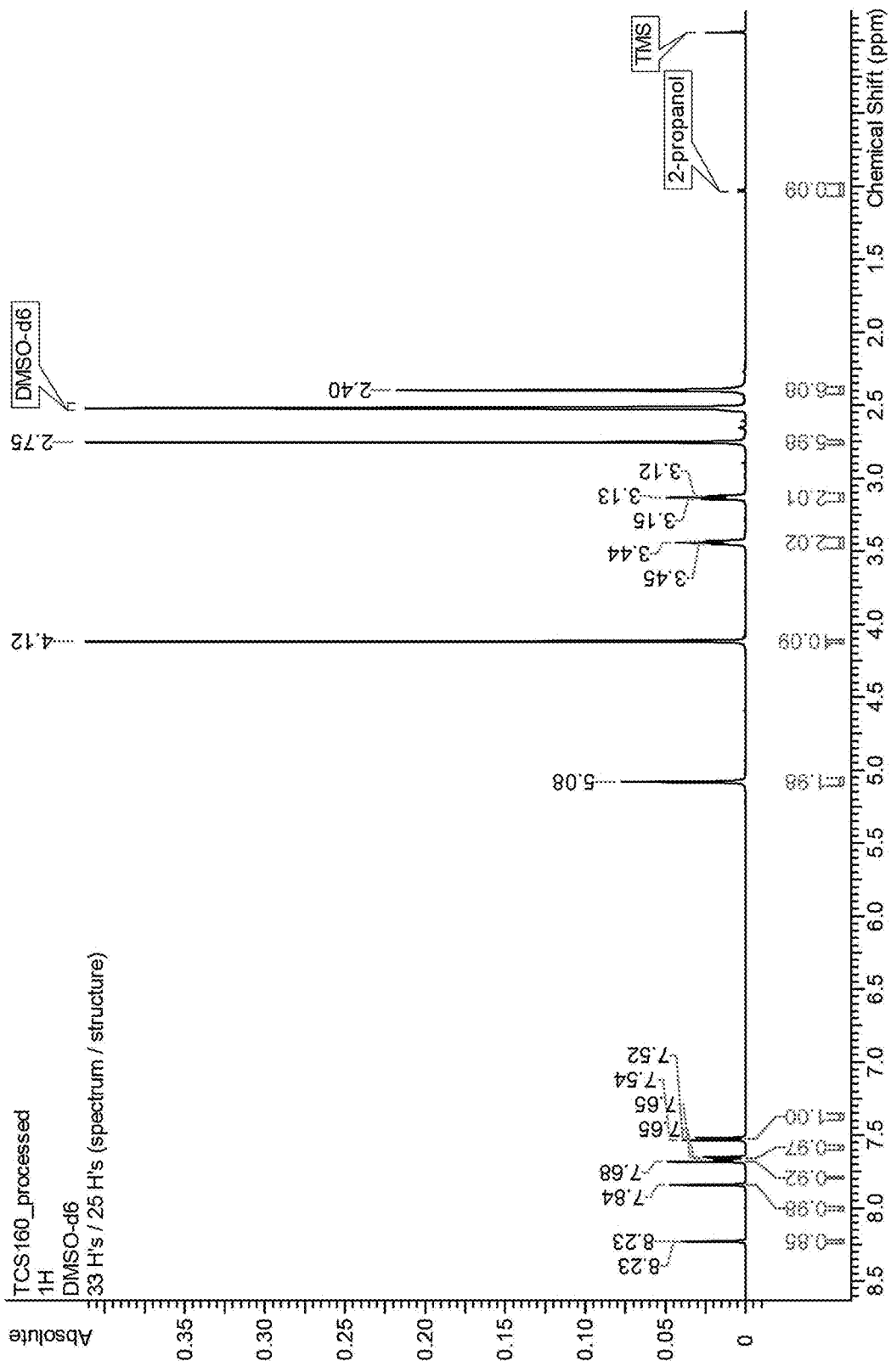
FIG. 14 shows $^1$H-NMR spectrum of the HCl salt (Exp. ID: TCS160). In addition to the API, signals of DMSO-$d_6$, 2-propanol and TMS were detected.
Figure 15A:
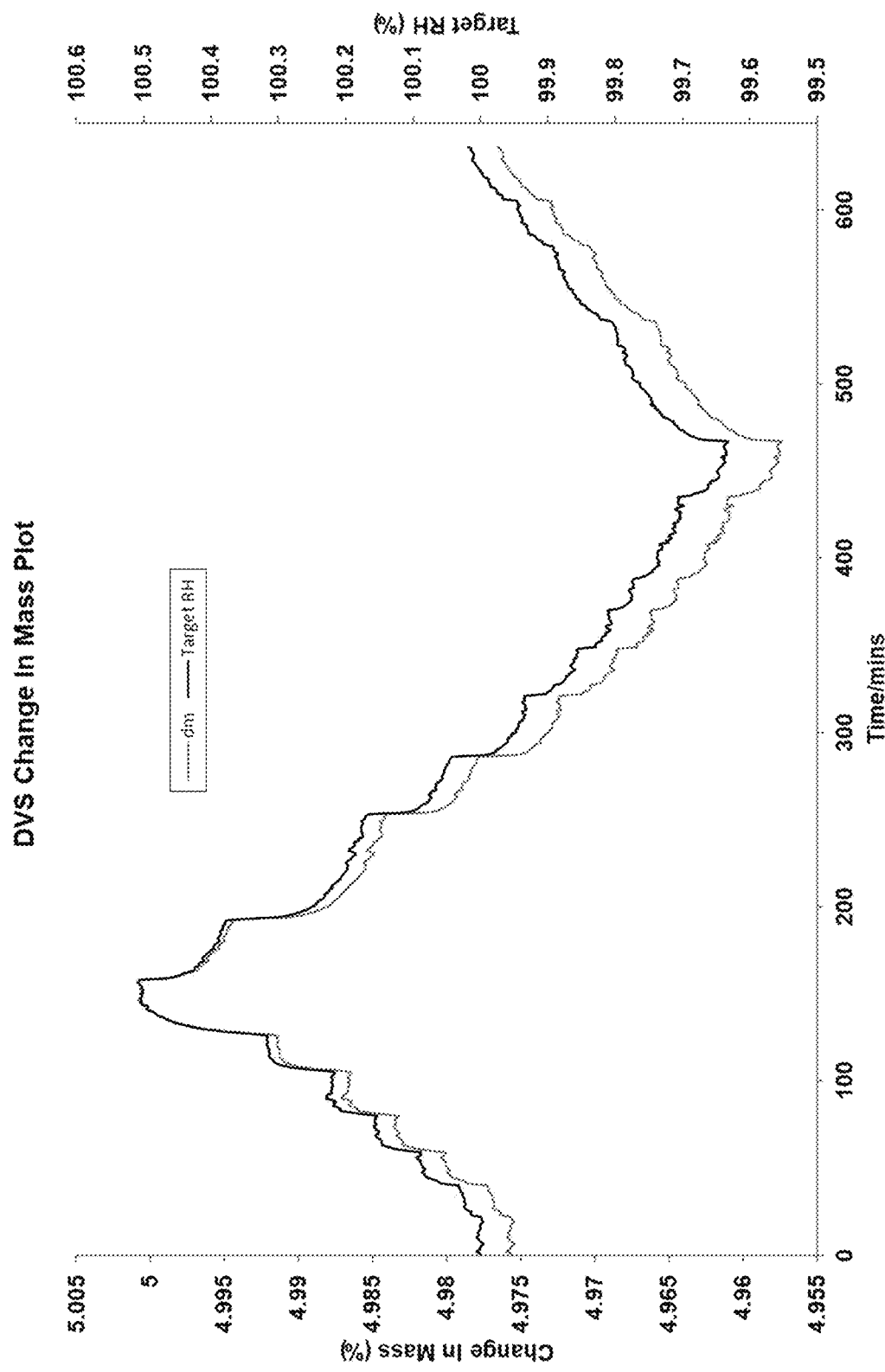
FIG. 15A and B shows Moisture Sorption Kinetic (A) and isotherm (B) plots for the HCl salt (Exp. ID: TCS160) with a first sorption cycle from 40% RH to 95% RH followed by desorption from 95% RH to 0% RH and sorption from 0% RH to 40% RH in steps of 10% RH with a minimum stage time of 10 min and maximum stage time of 6 hours.
Figure 15B:
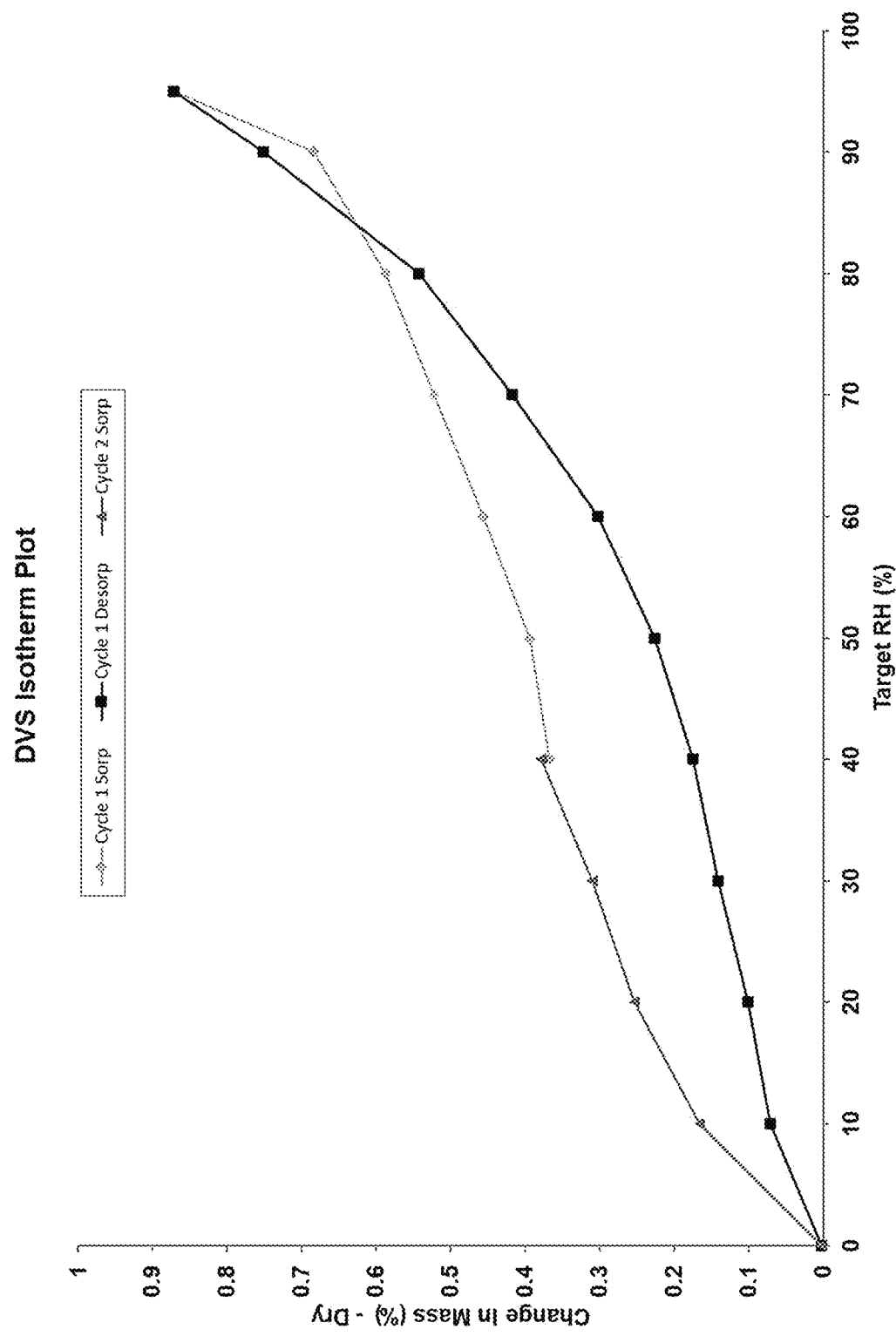

A set of 1.8 ml vials were prepared each containing 20 mg of Rabeximod free base. To each vial, a magnetic stir bar was added and 1.1 eq. of a selected acid. The acids were added as 1 M or 2 M aqueous solutions. In addition, a set of 1.8 ml vials were prepared containing API only. After that, 750 µl of a selected solvent was added. The vials were transferred to a Crystal16™ parallel crystallizer and the suspensions were stirred at 750 rpm. The experiments involving methanesulfonic acid, was subjected to a temperature profile depicted in FIG. 4. A slightly different temperature profile was applied for Hydrochloric acid and Malonic acid (FIG. 5).

All mixtures were heated from 25° C. to 50° C. after which the mixtures were stirred at 50° C. for 1 hour. After that, the temperature was reduced to 5° C. and the mixtures were stirred at 5° C. for 1 hour. Another heating-cooling cycle was applied in which the mixtures were again stirred for 1 hour at 50° C. The applied heating and cooling rates were −0.17° C./min. Depending on the type of acid used, the final steps of the temperature program involved the following:

In the experiments involving the hydrochloric acid, the temperature was set from 50° C. immediately to 25° C. After reaching 25° C., the mixtures were incubated without stirring for 3 days at 25° C.

After completion of the temperature program, the suspensions were subjected to centrifugation and the solids were isolated, dried under vacuum (50° C., 5 mbar, 18 h) and analyzed by HT-XRPD. The solvents from experiments in which no suspensions were obtained were completely evaporated. The mother liquors from most experiments in which a solid was formed were also evaporated to dryness. The resulting solids of the solvent evaporations were analyzed by HT-XRPD.

All solids were exposed to AAC (40° C./75% RH for 3 days) and remeasured by HT-XRPD. After that, 750 µl of a selected solvent was added. The vials were transferred to a Crystal16™ parallel crystallizer and the suspensions were stirred at 750 rpm at 50° C. for 18h after which the suspensions were subjected to centrifugation and the solids were isolated, dried under vacuum (50° C., 5 mbar, 18 h) and analyzed by HT-XRPD. The experimental conditions and results are shown below in Table 1 and Table 2 for the first and second set of experiments, respectively. The obtained XRPD patterns for the crystallinesalts made are shown in FIGS. 1 (HCl), 2 (Mao) and 3 (Mes).

TABLE 1

| Exp. ID | API mass (mg) | Solvent | API concentration (mg/ml) | Cl | API:Cl (1:x) | Solid phase | Solid phase (AAC) | Liquid phase | Liquid phase (AAC) |
|---|---|---|---|---|---|---|---|---|---|
| TCS4 | 19.7 | AcN | 26.3 | Mes | 1.1 | Mes | Mes | — | — |
| TCS9 | 20.3 | MeOH | 27.1 | Mes | 1.1 | — | — | Mes | Mes |
| TCS14 | 20.4 | EtOH | 27.2 | Mes | 1.1 | — | — | Mes | Mes |
| TCS19 | 20.4 | IPA | 27.2 | Mes | 1.1 | Mes | Mes | — | — |
| TCS24 | 19.6 | THF | 26.1 | Mes | 1.1 | — | Mes | — | — |
| TCS29 | 20.6 | Ace | 27.5 | Mes | 1.1 | Mes | Mes | — | — |

Experimental conditions and results of the methanesulfonic acid. In all experiments, 750 μl of solvent was used. Counterion (Cl) abbreviations denote pure counterions whereas counterions with a number denote novel salt forms. After subjecting suspensions of API:Cl to thermocycles (TCS experiments) or isothermal conditions (Ssm experiments), the solids were isolated, dried (5 mbar, 50° C., 18 h) and analyzed by XRPD. In some experiments, the liquid phases were dried and the resulting solids were analyzed by XRPD. Most solids were subjected to AAC (40° C., 75% RH, 3 days) and remeasured by XRPD.

TABLE 2

| Exp. ID | API mass (mg) | Solvent | API concentration (mg/ml) | Cl | API:Cl (1:x) | Solid phase | Solid phase (AAC) | Liquid phase | Liquid phase (AAC) |
|---|---|---|---|---|---|---|---|---|---|
| TCS39 | 17.0 | IPA | 22.7 | HCl | 1.1 | HCl | HCl1 | HCl1 (ly) | HCl1 (ly) |
| TCS105 | 18.2 | THF | 24.3 | Mao | 1.1 | Mao + Form 1 | Form 1 pc | Form 1 (ly) | Form 1 (ly) |
| TCS144 | 15.5 | Ace | 20.7 | Mao | 1.1 | Mao | Mao | — | — |

Experimental conditions and results of the hydrochloride and malonic acid salt crystallization experiments. In all experiments, 750 μl of solvent was used. Counterion (Cl) abbreviations denote pure counterions whereas counterions with a number denote novel salt forms. After subjecting suspensions of API:Cl to thermocycles, the solids were isolated, dried (5 mbar, 50° C., 18 h) and analyzed by XRPD. The liquid phases were dried, and the resulting solids were analyzed by XRPD. Most solids were subjected to AAC (40° C., 75% RH, 3 days) and remeasured by XRPD.

Table 3 shows an overview of the salt forms obtained in the present study. The solubility of the salts in water at RT was estimated by adding water to the salt until the salt dissolved. All salts showed higher solubilities than the freebase (<0.005 mg/ml), as indicated by the way that the salts interacted with water. The freebase showed no sign of dissolution whereas all salts became a good solution in water. From the TGMS data it was estimated whether the salts are stochiometric hydrates or not.

TABLE 3

| Counterion | Salt form | Salt form after AAC | Solubility in water (mg/ml) | TGMS (water %) | Water:API (x:1) | Water uptake | Form after DVS |
|---|---|---|---|---|---|---|---|
| Methanesulfonic acid | Mes | Mes | 13.3 | 4.9 | 1.6 | 12.2 | Mes1 |
| Hydrochloric acid | HCl | HCl | 2.0-5.7 | 0.0 | 0.0 | | |
| Malonic acid | Mao | Mao | 5.5-10.2 | 0.1* | 0.0 | | |

* = thermal decomposition <150° C.
AAC refers to Accelerated aging conditions (3 days at 40° C. and 75% RH).

EXAMPLE 2: SCALE-UP EXPERIMENTS

The preparation of selected salts was performed at a larger scale to obtain additional material for further analytical characterization. The experiments were started either with 100 mg (1$^{st}$ set) or with 1200 mg (2$^{nd}$ set) of Rabeximod free base (Form 1, starting material). For the 100 mg experiments, the starting material was weighed into 8 ml vials which contained magnetic stir bars. The 1200 mg experiments were performed in a 100 ml Mettler Toledo Multi-Max™ crystallization setup which was equipped with overhead stirrers. The selected acids were added as 1 M or 2 M aqueous solutions. After that, the selected solvent was added and stirring was applied at a stirring rate of 750 rpm. The stirred suspensions were subjected to a temperature profile like the profile described in FIG. 5 but with a final 9-hour incubation period at 25° C.

After the temperature cycles, the suspensions were filtered using vacuum filtration in combination with a Büchner funnel. The solids were dried under ambient conditions for 18 h and a sample was measured by XRPD. The solids obtained from experiments TCS32-34 and TCS36 were further dried for 18h at 50° C. and 5 mbar. The solids obtained from experiment TCS35 were further dried for 4 days at RT and 200 mbar whereas the solids obtained from experiment TCS37 were further dried for 4 days at 50° C. and 5 mbar.

Experimental conditions and XRPD results for the scale-up experiments of selected Rabeximod salts are shown in table 4. Counterion (Cl) abbreviations denote pure counterions whereas counterions with a number denote novel salt forms of the API. "AAC" means that the sample was exposed to 40° C./75% RH for 3 days before analysis by XRPD. The materials were dried under vacuum conditions and those details are described below.

Quantitative Solubility Determination

The thermodynamic solubility of Rabeximod free base (Form 1) was determined in 3 different USP buffers (50 mM) ranging from pH 1.2 to pH 7.4 and in water (Exp. ID: QSA21-24) by the shake-flask method at 25° C. ( Table ). Approximately 30 mg was added to approximately 1 ml of the selected buffer and the resulting suspension was equilibrated at RT for 4 hours under continuous stirring. After 15 min and after 4 h of stirring, the pH of the solution was recorded. Upon completion of the equilibration time, the suspensions were centrifuged. The solution was filtered and diluted before LCMS analysis to determine the API concentration in solution. The residue was dried under vacuum and the obtained dried solids were analyzed by XRPD. A standard LC calibration curve was prepared, and the diluted mother liquors were measured to determine the API concentration.

The solubility of the freebase (Form 1) and salts prepared by scale-up was determined in water at room temperature. Suspensions were stirred for 18 h after which the liquid phase was isolated and measured by LCMS against a calibration line. The solids were dried and measured by XRPD to determine the solid form. The results are summarized in the table below. The lowest solubility was determined for the freebase (Form 1). The signal was lower than the calibration line and therefore the solubility was determined to be <0.005 mg/ml. The two anhydrous salts Mao1 and HCl1 had a solubility of 5.3 mg/ml and 5.5 mg/ml in water, respectively. The highest solubility was tested for Mes1 showing solubility of 13.3 mg/ml. The experimental details are described in table 5.

Table 5. Experimental details and results of the solubility determination for Rabeximod free base Form 1) as well as salt Mes1 in water and in 3 buffers with pH range 1.2-7.4. The pH of the solutions after 15 minutes and 4 hours are

TABLE 4

| Exp. ID | API Mass (mG) | Counterion | API:Cl (1:x) | Solvent | Solvent (ml) | API concentration (mg/ml) | ioslated yield (g) | ioslated Yield (%) | crystallinity (XRPD) Ambient | Vacuum | Vacuum AAC |
|---|---|---|---|---|---|---|---|---|---|---|---|
| TCS31 | 100.8 | Mes | 1.1 | Acetone | 3.8 | 26.7 | — | — | High | | high |
| TCS35 | 1202.3 | Mes | 1.1 | Acetone | 42.0 | 28.6 | 1.4 | 70.2 | High | high$^a$ | |
| TCS160 | 1198.9 | HCl | 1:1 | IPA | 45.0 | 26.6 | 1.2 | 84.2 | High | high$^b$ | |
| TCS161 | 1201.8 | Mao | 1:1 | IPA | 45.0 | 26.7 | 1.4 | 74.1 | high | high$^b$ | |

$^a$4 days at RT and 200 mbar; $^b$1 day at RT and 5 mbar.

Results of TGMS, DSC, LCMS, $^1$H-NMR, $^{13}$C-NMR-APT and moisture sorption analyses of the MES and HCl salts are shown in FIGS. 6-11 and 7-15 respectively. These results confirm that the respective products were highly pure and have favorable stability attributes.

EXAMPLE 3: SOLUBILITY

Qualitative Solubility Determination

The solubility of a selection of salts from the salt screen was estimated at room temperature in water. To approximately 2 mg of salt, solvent aliquots were added in steps of 50 µl until the material was dissolved as observed visually by the naked eye.

reported. The solubility was determined after 4h equilibration by measuring the liquid phase with LCMS against a calibration line.

| Exp. ID | Form (from Exp. ID) | Medium | PH buffer | pH after 15 min | pH after 4 h | Solubility (mg/ml) |
|---|---|---|---|---|---|---|
| QSA9 | Form 1 (SM) | HCl | 1.2 | 1.2 | 1.4 | 0.013 |
| QSA10 | Mes (TCS35) | | | 1.5 | 1.3 | 0.014 |
| QSA13 | Form 1 (SM) | Phosphate | 6.5 | 6.0 | 6.2 | 0.005* |
| QSA14 | Mes (TCS35) | buffer | | 4.2 | 4.4 | 0.042 |
| QSA17 | Form 1 (SM) | Phosphate | 7.4 | 7.3 | 7.4 | <LOD |
| QSA18 | Mes (TCS35) | buffer | | 6.0 | 6.1 | 0.003* |
| QSA21 | Form 1 (SM) | Water | — | — | — | <0.005 |
| QSA22 | Mes (TCS35) | | | | | 13.26 |

-continued

| Exp. ID | Form (from Exp. ID) | Medium | PH buffer | pH after 15 min | pH after 4 h | Solubility (mg/ml) |
|---|---|---|---|---|---|---|
| QSA23 | HCl (TCS160) | | | | | 5.45 |
| QSA24 | Mao (TCS161) | | | | | 5.26 |

EXAMPLE 4: PHARMACOKINETIC CHARACTERIZATION

Formulation Preparation

IV formulations were prepared on the day of dosing. The formulations were prepared by weighing the compound into brown glass vial; on the day of dosing ClinOleic 20% intravenous fat emulsion (200 µg/mL, Tamro) was added into tubes (1,5 mg/mL in 20% ClinOleic). Formulations were homogenized 5 minutes before dosing. IV formulations were administered within 5 hours after preparation.

PO formulations were prepared day before administration. The formulations were prepared by formulating the test items in PO vehicle (6 mg/ml in 0.45% (v/v) Tween 80-0.11% (w/v) sodium carboxy methylcellulose (CMC) in tap water). The suspensions were mixed with vortex and stored refrigerated (+4° C.) over night. On the day of dosing formulations were homogenized 15 minutes before dosing.

Animal Experiment

Naïve animals were used in the study (see Table 6). They were housed in individually ventilated (IVC)-cages in groups of six mice. The cages were provided with aspen bedding (4HP and PM90L, Tapvei, Estonia) and paper strands (Sizzlenest, Datesand, UK) as nesting material, and a paper pulp cabin and red polycarbonate cylinder (Datesand, UK) as cage enrichment. The temperature (22±2° C.), humidity (55±10%) and air exchange rate (75 times/h) of the IVC-cages and 12/12-h light/dark cycle (500 lux lighting on at 6 a.m., 1.5 lux lighting on at 6 p.m.) of the animal holding room were automatically controlled and maintained. Animals were allowed to acclimatize to the site for at least five days prior to the study. Animals had ad libitum access to food (SDS diets, RM1 (E) 801002, Special Diets Services, UK) and tap water at all times, and their welfare was assured with daily observations.

TABLE 6

Animals and treatment groups.

| Animals | |
|---|---|
| Strain, species | CD-1 mice |
| Gender | male |
| Age | 5 weeks; born 14 Dec. 2020 |
| Weight* | 25-32 g |
| Source | Charles River Laboratories, Germany |
| | Sampling |
| Time points (i.v.) | 0.083, 0.167, 0.25, 0.5, 1,2, 4, 8 and 24 h |
| Time points (p.o.) | 0.083, 0.167, 0.25, 0.5, 1,2, 4, 8 and 24 h |
| Sampling method | saphenous venepuncture / cardiac puncture |
| Sampling tube | K2EDTA tube |

| Treatment groups | | |
|---|---|---|
| Compound | Dose, route, volume | n/group |
| Rabeximod Form 1 | 3 mg/kg, IV, 2 ml/kg | 12 |
| Rabeximod Form 1 | 30 mg/kg, PO, 5 ml/kg | 12 |
| Mao1 | 3 mg/kg, IV, 2 ml/kg | 12 |

TABLE 6-continued

Animals and treatment groups.

| Compound | Dose, route, volume | n/group |
|---|---|---|
| Mao1 | 30 mg/kg, PO, 5 ml/kg | 12 |
| HCl | 3 mg/kg, IV, 2 ml/kg | 12 |
| HCl | 30 mg/kg, PO, 5 ml/kg | 12 |
| Mes1 | 3 mg/kg, IV, 2 ml/kg | 12 |
| Mes1 | 30 mg/kg, PO, 5 ml/kg | 12 |
| Blank, no compound | No dosing | 10 |

*All animals were weighed one day before dosing.

Study compounds were administered via the specified route and the times of dosing and blood sampling were recorded. Within 30 min following the sampling, the blood was centrifuged for plasma separation (room temperature; 10 min; 2700 G). The plasma samples were transferred into plastic tubes, frozen and stored at −20° C. until analysis. Clinical signs and general behavior of the animals were recorded, when necessary.

Pharmacokinetic Analysis

The pharmacokinetic parameters were calculated using Phoenix 64 (Build 6.4.0.768) WinNonlin (version 6.4) software, using non-compartmental methods (NCA). Nominal doses were used for all animals. The terminal phase half-life ($T_{1/2}$) was calculated by least-squares regression analysis of the terminal linear part of the log concentration—time curve. The area under the plasma concentration—time curve (AUC) was determined with the linear trapezoidal rule for increasing values and log trapezoidal rule for decreasing values up to the last measurable concentration ($AUC_{0-last}$), and extrapolation of the terminal elimination phase to infinity was used when possible; the following criteria were used:

Minimum of 3 points (not including $C_{max}$) used to calculate lambda (with $R^2$ adjusted >0.85)

$T_{1/2}$ shorter than the time-span used to calculate lambda $AUC_{inf\_Extrap}$ % <20%

The maximum plasma concentration ($C_{max}$) and the time to reach $C_{max}$ ($t_{max}$) were derived directly from the plasma concentration data.

Figure 16:
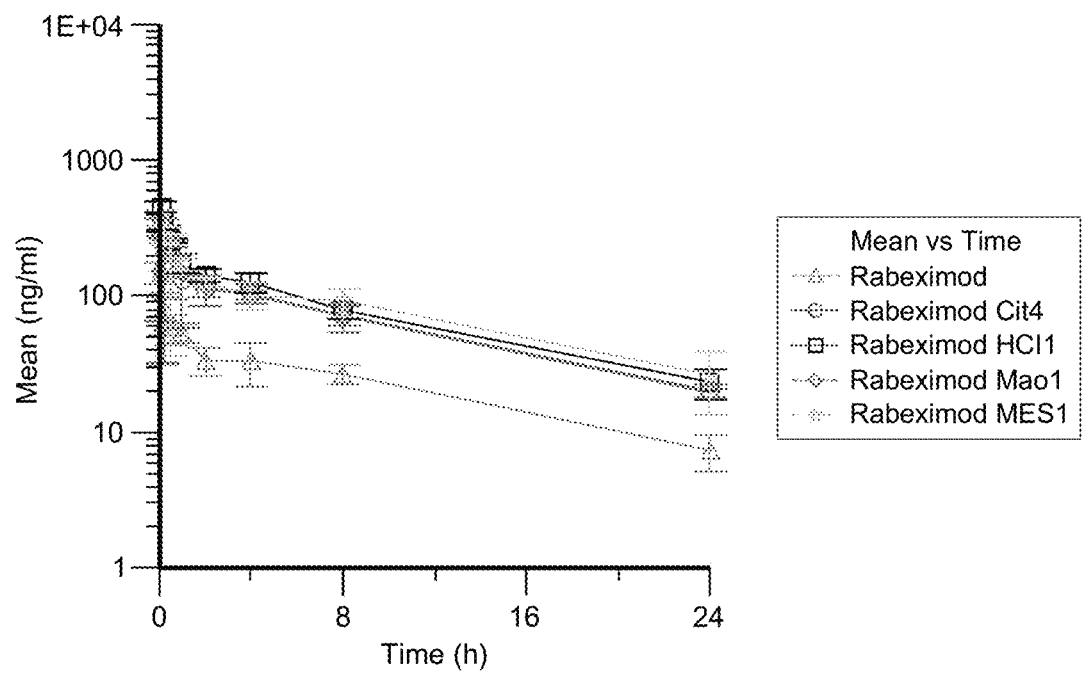
FIG. 16 shows the mean (±SD) plasma concentration vs. time profiles for Rabeximod and Rabeximod salts after i.v. administration to male CD1 mice (n=3 per time point) at nominal doses of 3.00 mg/kg.
Figure 17:
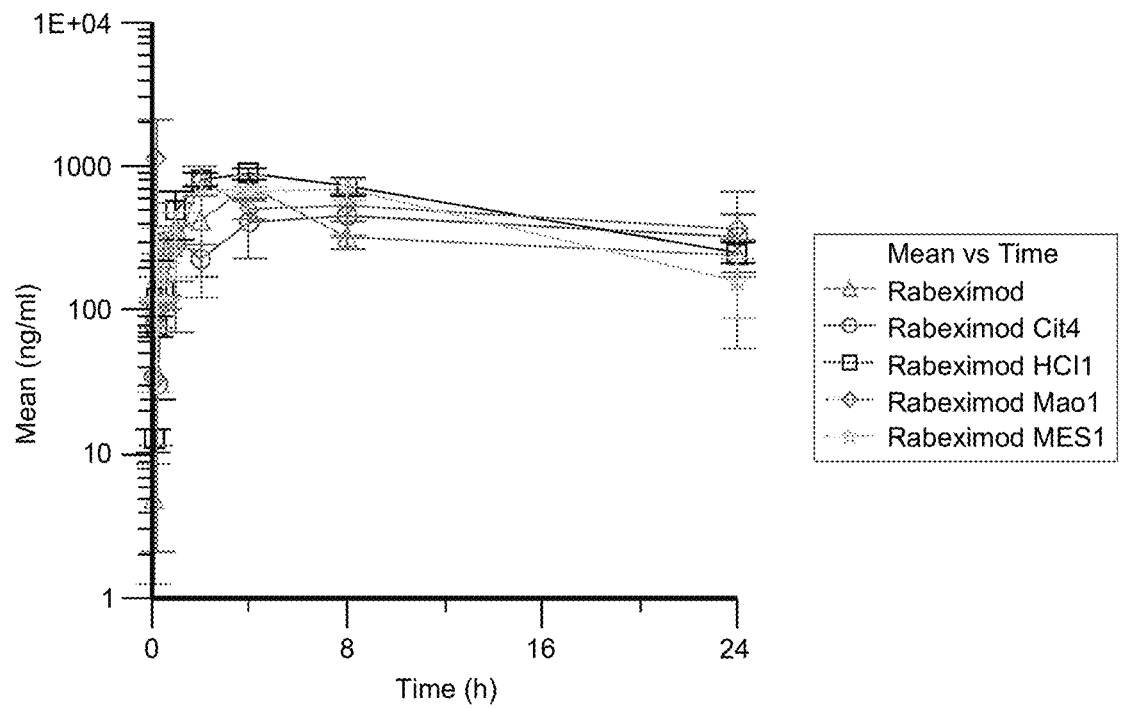
FIG. 17 shows the mean (±SD) plasma concentration vs. time profiles for Rabeximod and Rabeximod salts after p.o. administration to male CD1 mice (n=3 per time point) at nominal doses of 30.00 mg/kg.

The mean (±SD) plasma concentration vs. time profiles for Rabeximod and Rabeximod salts after i.v. and p.o. administration are shown in FIGS. 16 and 17. These figures illustrate the following findings.

After i.v. administration of Rabeximod as free base at 3.00 mg/kg, plasma concentrations peaked at the first, 0.0833 h sample time post-dosing with the mean $C_{max}$ of 150 ng/ml and the mean $C_0$ of 351 ng/ml. The values for $AUC_{0-inf}$ and $T_{1/2}$ were 681 h*ng/ml and 8.99 h, respectively. The values for CL and $V_{ss}$ of were 73.4 ml*min/kg (61.2% of mouse liver blood flow (120 ml/min/kg; Ring et all, 2011) and 49.4 l/kg, respectively. After p.o. administration of Rabeximod at 30.0 mg/kg, plasma concentrations peaked at 4.00 h post-dose with the mean $C_{max}$ of 728 ng/ml. The value for $AUC_{0-last}$ was 8330 h*ng/ml.

After i.v. administration of Rabeximod HCl at 3.00 mg/kg, plasma concentrations peaked at the first, 0.0833 h sample time post-dosing with the mean $C_{max}$ of 454 ng/ml and the mean $C_0$ of 600 ng/ml. The values for $AUC_{0-inf}$ and $T_{1/2}$ were 2220 h*ng/ml and 8.43 h, respectively. The values for CL and $V_{ss}$ were 22.6 ml*min/kg (18.8% of mouse liver blood flow (120 ml/min/kg) and 14.2 l/kg, respectively. After p.o. administration of Rabeximod HCl at 30.0 mg/kg, plasma concentrations peaked at 4.00 h post-dose with the mean $C_{max}$ of 893 ng/ml. The value for $AUC_{0-last}$ was 13 700 h*ng/ml.

After i.v. administration of Rabeximod Mao at 3.00 mg/kg, plasma concentrations peaked at the first, 0.0833 h sample time post-dosing with the mean $C_{max}$ of 355 ng/ml and the mean $C_0$ of 390 ng/ml. The values for $AUC_{0-inf}$ and $T_{1/2}$ were 1870 h*ng/ml and 8.43 h, respectively. The values for CL and $V_{ss}$ were 26.8 ml*min/kg (22.3% of mouse liver blood flow (120 ml/min/kg) and 16.9 l/kg, respectively. After p.o. administration of Rabeximod Mao at 30.0 mg/kg, plasma concentrations peaked at 0.17 h post-dose with the mean $C_{max}$ of 1140 ng/ml. The value for $AUC_{0-last}$ was 11 400 h*ng/ml.

After i.v. administration of Rabeximod Mes at 3.00 mg/kg, plasma concentrations peaked at the first, 0.0833 h sample time post-dosing with the mean $C_{max}$ of 383 ng/ml and the mean $C_0$ of 507 ng/ml. The values for $AUC_{0-inf}$ and $T_{1/2}$ were 2320 h*ng/ml and 9.80 h, respectively. The values for CL and $V_{ss}$ were 21.5 ml*min/kg (17.9% of mouse liver blood flow (120 ml/min/kg) and 15.9 l/kg, respectively. After p.o. administration of Rabeximod Mes at 30.0 mg/kg, plasma concentrations peaked at 2.00 h post-dose with the mean $C_{max}$ of 707 ng/ml. The values for $AUC_{0-last}$ and $T_{1/2}$ were 11 600 h*ng/ml and 8.93 h, respectively.

In conclusion, when the values for values for $AUC_{0-last}$ are compared, the rank order for exposure after oral administration is as follows: Rabeximod HCl>Rabeximod Mes>Rabeximod Mao>Rabeximod.

The invention claimed is:

1. A compound selected from the group consisting of a HCl salt, a methane sulphonic acid (mesylate) salt and a malonic acid salt of the compound of formula (I)

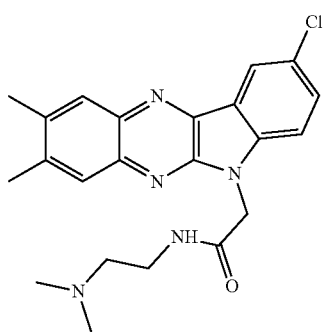

(I)

wherein the compound has a solubility in water at room temperature of at least 5 mg/ml.

2. The compound of claim 1, wherein the compound is a solid form.

3. The compound of claim 1, wherein the compound is a crystalline form.

4. The compound of claim 1, wherein the compound is selected from the group consisting of salts obtained by the reaction of Rabeximod with an acid selected from HCl, malonic acid and methane sulphonic acid.

5. A HCl salt of the compound of formula (I)

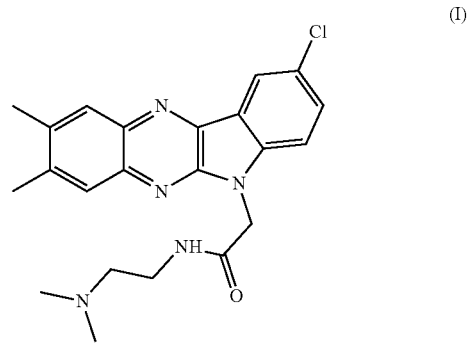 [SMILES: Cc1cc2nc3c4cc(Cl)ccc4n(CC(=O)NCCN(C)C)c3nc2cc1C]

(I)

wherein the HCl salt of the compound of formula (I) is in a crystalline form characterized by the following XRPD peaks:

| Peak number | 2θ° | d (Å) | Intensity[%] |
|---|---|---|---|
| 1 | 4.38 | 20.18 | 4 |
| 2 | 8.92 | 9.90 | 35 |
| 3 | 9.68 | 9.13 | 52 |
| 4 | 10.84 | 8.16 | 27 |
| 5 | 13.04 | 6.78 | 63 |
| 6 | 13.90 | 6.37 | 49 |
| 7 | 15.66 | 5.65 | 14 |
| 8 | 17.42 | 5.09 | 30 |
| 9 | 18.28 | 4.85 | 13 |
| 10 | 18.53 | 4.79 | 14 |
| 11 | 19.42 | 4.57 | 13 |
| 12 | 19.65 | 4.51 | 33 |
| 13 | 20.27 | 4.38 | 29 |
| 14 | 20.49 | 4.33 | 13 |
| 15 | 21.07 | 4.21 | 12 |
| 16 | 22.07 | 4.02 | 16 |
| 17 | 23.24 | 3.82 | 17 |
| 18 | 23.50 | 3.78 | 10 |
| 19 | 24.44 | 3.64 | 100 |
| 20 | 24.80 | 3.59 | 11 |
| 21 | 25.28 | 3.52 | 33 |
| 22 | 25.96 | 3.43 | 49 |
| 23 | 26.22 | 3.40 | 18 |
| 24 | 26.78 | 3.33 | 42. |

6. A methane sulphonic acid salt of the compound of formula (I)

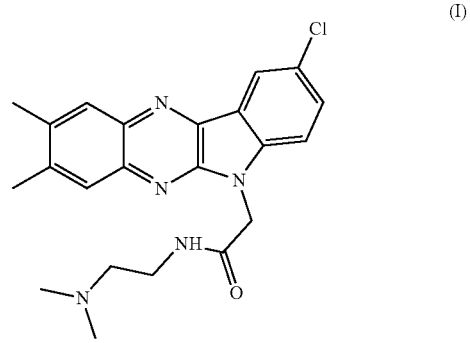 [SMILES: Cc1cc2nc3c4cc(Cl)ccc4n(CC(=O)NCCN(C)C)c3nc2cc1C]

(I)

wherein the methane sulphonic acid salt of the compound of formula (I) is in a crystalline form characterized by the following XRPD peaks:

| Peak number | 2θ° | d (Å) | Intensity[%] |
|---|---|---|---|
| 1 | 3.30 | 26.79 | 43 |
| 2 | 8.04 | 10.98 | 38 |
| 3 | 8.65 | 10.22 | 64 |
| 4 | 10.45 | 8.46 | 21 |
| 5 | 12.48 | 7.09 | 12 |
| 6 | 12.91 | 6.85 | 28 |
| 7 | 15.00 | 5.90 | 5 |
| 8 | 16.15 | 5.48 | 18 |
| 9 | 17.40 | 5.09 | 14 |
| 10 | 19.10 | 4.64 | 14 |
| 11 | 20.49 | 4.33 | 21 |
| 12 | 20.72 | 4.28 | 25 |
| 13 | 24.79 | 3.59 | 100 |
| 14 | 27.39 | 3.25 | 24. |

7. A malonic acid salt of the compound of formula (I)

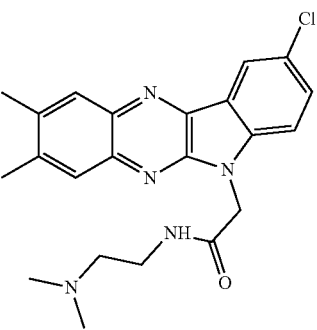

(I)

wherein the malonic acid salt of the compound of formula (I) in a crystalline form characterized by the following XRPD peaks:

| Peak number | 2θ° | d (Å) | Intensity[%] |
|---|---|---|---|
| 1 | 6.37 | 13.87 | 64 |
| 2 | 7.12 | 12.41 | 54 |
| 3 | 8.62 | 10.25 | 56 |
| 4 | 9.96 | 8.87 | 9 |
| 5 | 10.39 | 8.51 | 20 |
| 6 | 10.88 | 8.13 | 11 |
| 7 | 12.64 | 7.00 | 2 |

-continued

| Peak number | 2θ° | d (Å) | Intensity[%] |
|---|---|---|---|
| 8 | 13.08 | 6.76 | 4 |
| 9 | 13.54 | 6.54 | 4 |
| 10 | 14.25 | 6.21 | 53 |
| 11 | 14.50 | 6.10 | 22 |
| 12 | 15.46 | 5.73 | 6 |
| 13 | 15.69 | 5.64 | 5 |
| 14 | 16.25 | 5.45 | 6 |
| 15 | 16.67 | 5.31 | 6 |
| 16 | 17.26 | 5.13 | 5 |
| 17 | 18.49 | 4.80 | 18 |
| 18 | 18.86 | 4.70 | 29 |
| 19 | 19.13 | 4.64 | 48 |
| 20 | 19.54 | 4.54 | 31 |
| 21 | 21.66 | 4.10 | 16 |
| 22 | 25.36 | 3.51 | 100 |
| 23 | 21.55 | 4.12 | 24. |

8. The compound of claim 1, wherein the compound is a salt that is obtained by a process comprising:
   a) adding HCl, methane sulphonic acid or malonic acid as a suspension or as a solution, to the free base of rabeximod, as a solid, as a suspension or as a solution, to provide a solution or a suspension of the corresponding salt; and
   b) obtaining the salt as a solid by precipitation or crystallization by cooling, by evaporation of solvent, by addition of an antisolvent, by addition to an antisolvent, or by addition of a co-crystallizing agent, followed by filtration or centrifugation and optionally purifying the salt.

9. The compound of claim 1, wherein the compound has a solubility in water at room temperature of 5-15 mg/ml.

10. A pharmaceutical composition comprising the compound of claim 1, and optionally a pharmaceutically acceptable additive.

11. A compound of claim 1 for use in a method for treating a human subject, suffering from or diagnosed with rheumatoid arthritis.

12. A method for treatment of a human subject, suffering from or diagnosed with rheumatoid arthritis comprising administering to the mammal subject an amount of a compound of claim 1 effective to treat said rheumatoid arthritis.

* * * * *